(12) United States Patent
Tanikawa et al.

(10) Patent No.: US 11,194,145 B2
(45) Date of Patent: Dec. 7, 2021

(54) IMAGE REPRODUCING DEVICE AND OBSERVATION SYSTEM FOR SELECTING IMAGES USING TAG INFORMATION ATTACHED IN ACCORDANCE WITH INFORMATION THAT OPERATION IS PERFORMED ON SAMPLE AND INPUT WHEN AT LEAST ONE OF IMAGES IS ACQUIRED

(71) Applicant: OLYMPUS CORPORATION, Tokyo (JP)

(72) Inventors: Yohei Tanikawa, Hino (JP); Shinichi Takimoto, Hachioji (JP); Masakazu Fujii, Tokyo (JP); Taiji Mine, Machida (JP); Takayuki Nakatomi, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 124 days.

(21) Appl. No.: 16/677,809

(22) Filed: Nov. 8, 2019

(65) Prior Publication Data
US 2020/0073104 A1    Mar. 5, 2020

Related U.S. Application Data

(63) Continuation of application No. PCT/JP2017/017583, filed on May 9, 2017.

(51) Int. Cl.
*G02B 21/00* (2006.01)
*G02B 21/36* (2006.01)

(52) U.S. Cl.
CPC ....... *G02B 21/0084* (2013.01); *G02B 21/367* (2013.01); *G02B 21/368* (2013.01)

(58) Field of Classification Search
CPC  G02B 21/0084; G02B 21/367; G02B 21/368; G02B 21/00; G02B 21/0004;
(Continued)

(56) References Cited

U.S. PATENT DOCUMENTS

2017/0177789 A1\*  6/2017  Iga .......................... G06F 16/00

FOREIGN PATENT DOCUMENTS

JP     2002-085054 A     3/2002
JP     2005-167822 A     6/2005
(Continued)

OTHER PUBLICATIONS

English translation of JP2008136415A, retrieved May 7, 2021. (Year: 2008).\*

(Continued)

*Primary Examiner* — Arnel C Lavarias
(74) *Attorney, Agent, or Firm* — Scully, Scott, Murphy & Presser, P.C.

(57) ABSTRACT

An image reproducing device includes one or more processors. The processor acquires image group data including a plurality of images and tag information on at least one tag. The images relate to a biological sample along time series. The tag information relates to an operation on the biological sample and is associated with at least part of the images. The processor selects from the plurality of images using the tag information, images to be reproduced along the time series as reproduction selected images. The processor outputs to a display, data relating to the images for the reproduction selected images to be reproduced along time series.

10 Claims, 21 Drawing Sheets

(58) Field of Classification Search
CPC .... G02B 21/008; G02B 21/36; G02B 21/365; C12M 1/005; C12M 1/34; C12M 1/3446; C12M 1/3476; C12M 1/36
USPC ................................. 359/368, 362, 363, 369
See application file for complete search history.

(56) References Cited

FOREIGN PATENT DOCUMENTS

| | | | |
|---|---|---|---|
| JP | 2008-139488 A | 6/2006 | |
| JP | 2008-136415 A | 6/2008 | |
| JP | 2008-139489 A | 6/2008 | |
| JP | 2017-062611 A | 3/2017 | |
| WO | WO 2007/132870 A1 | 11/2007 | |
| WO | WO 2015/159753 A1 | 10/2015 | |

OTHER PUBLICATIONS

Japanese Office Action dated Aug. 4, 2020 in Japanese Patent Application No. 2019-516777.
International Search Report dated Jul. 18, 2017 issued in PCT/JP2017/017583.
English translation of International Preliminary Report on Patentability dated Nov. 21, 2019, together with the Written Opinion received in related International Application No. PCT/JP2017/017583.

* cited by examiner

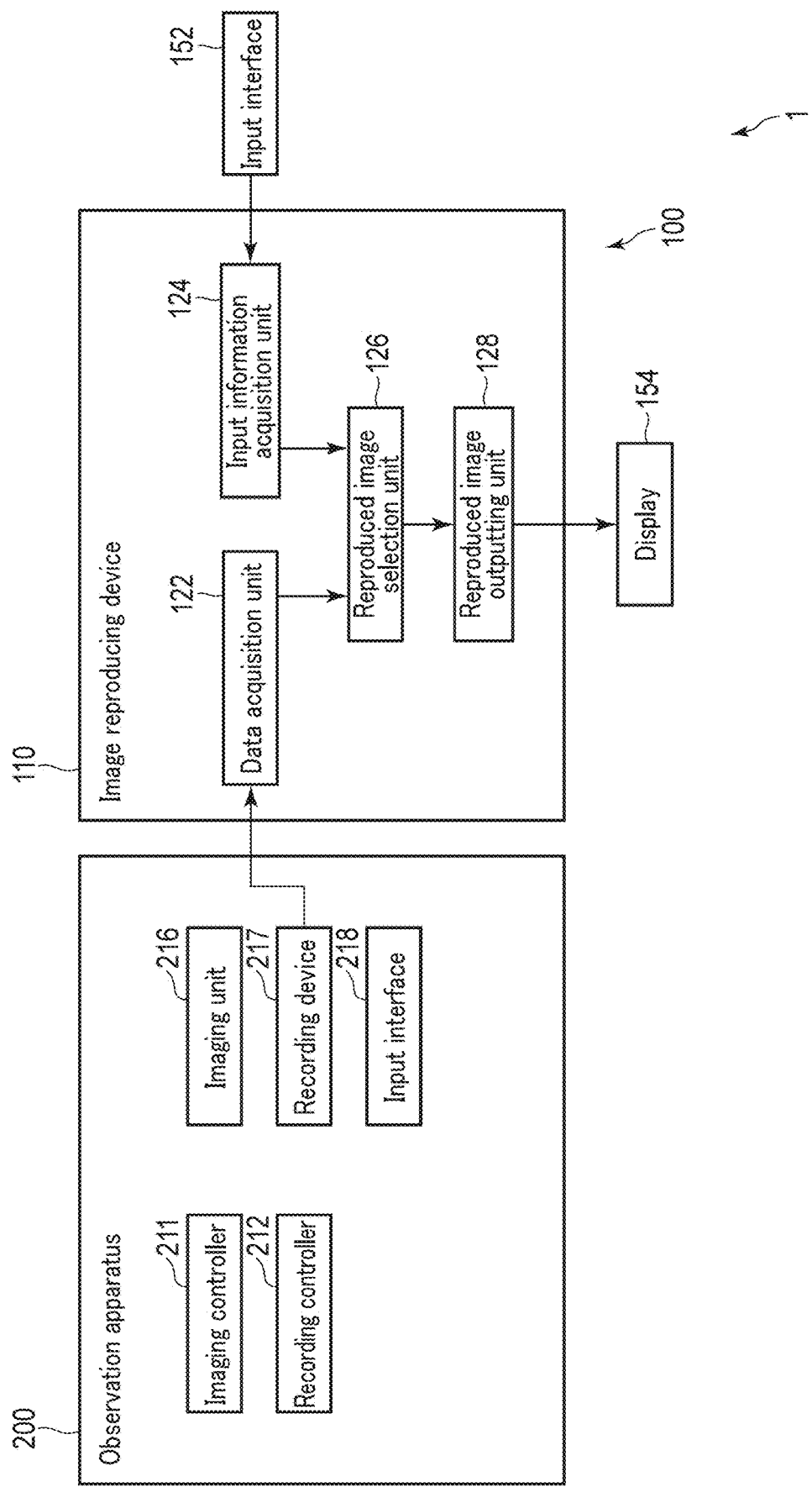
F I G. 2

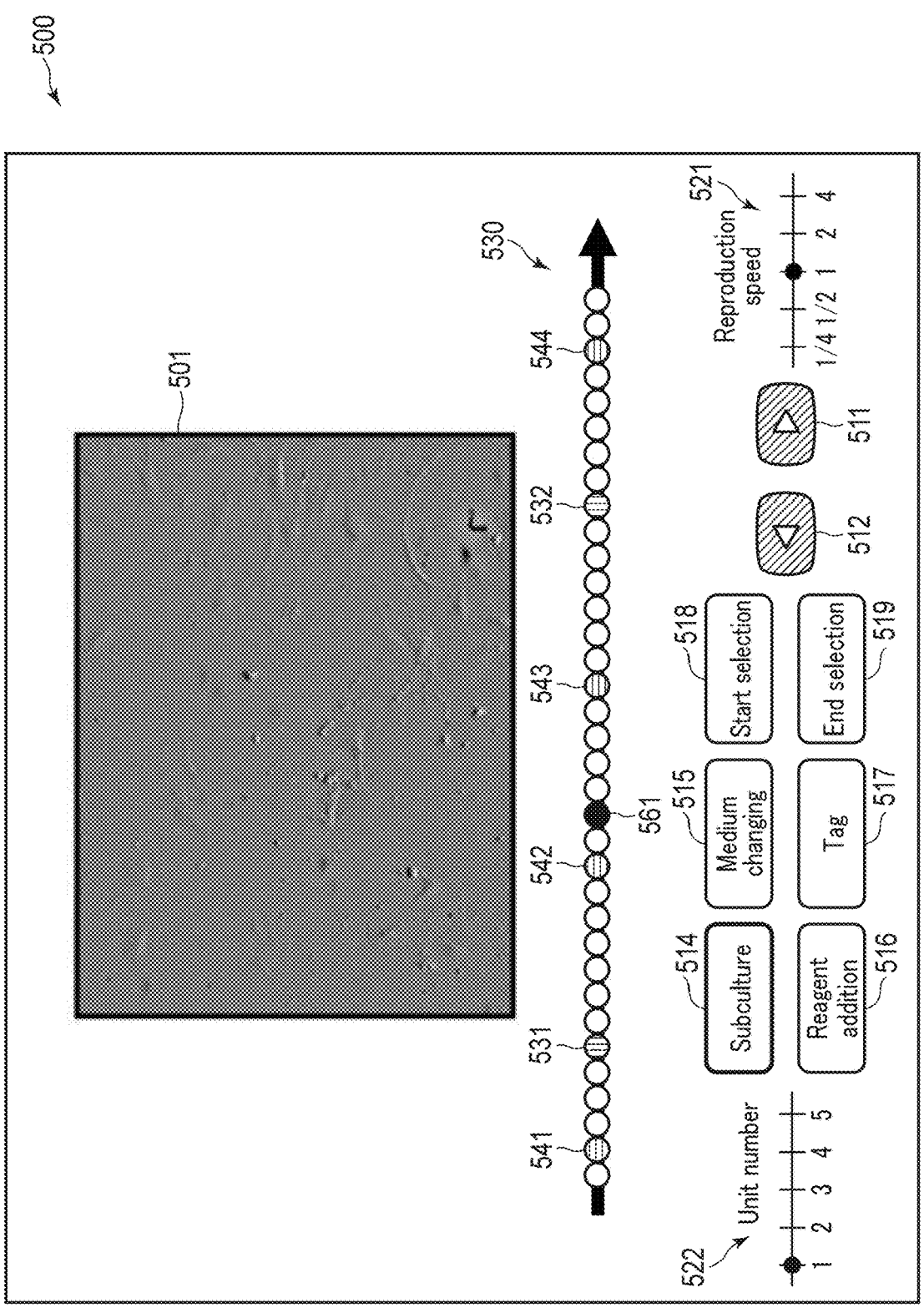
F I G. 4A

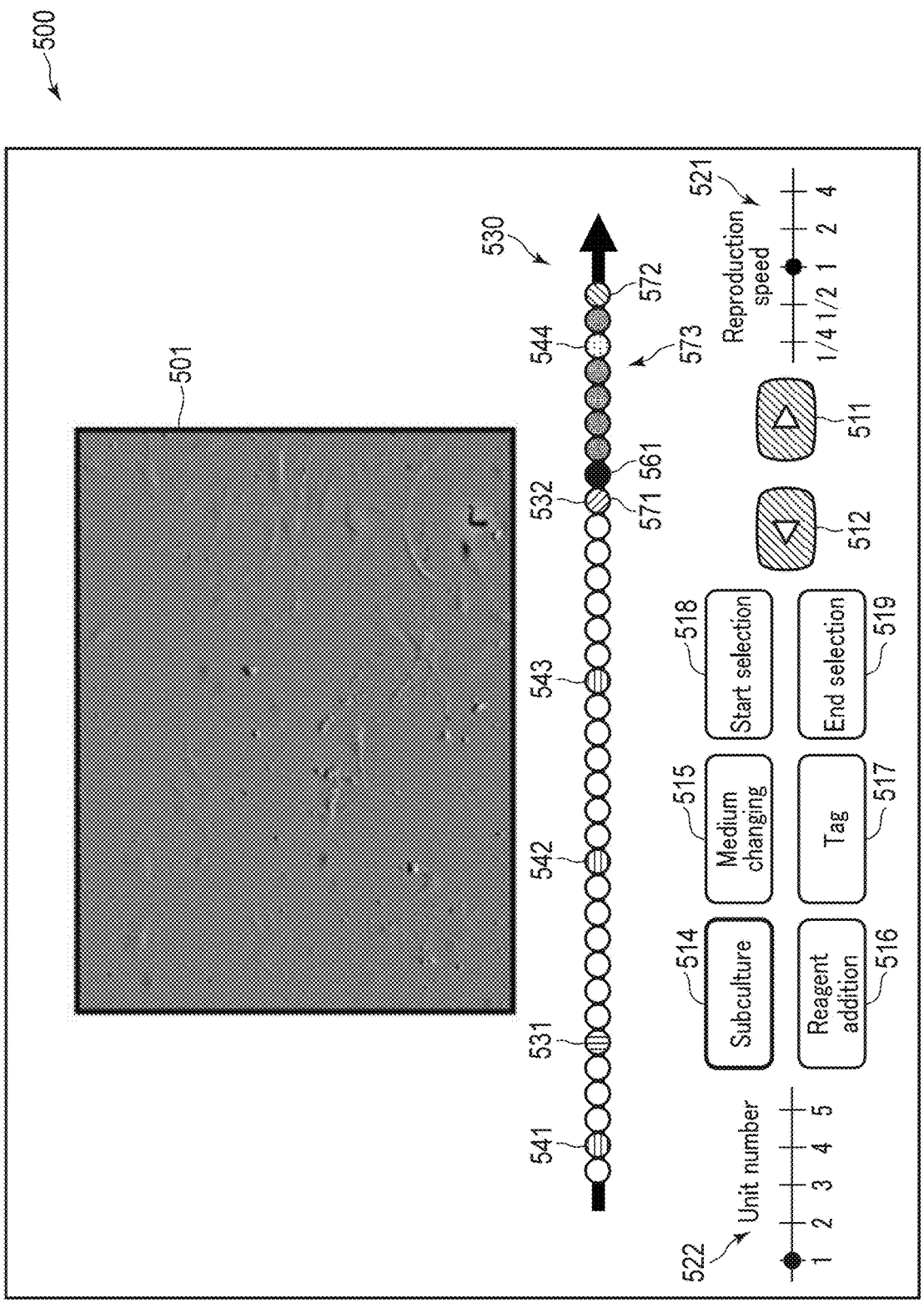
F I G. 5B

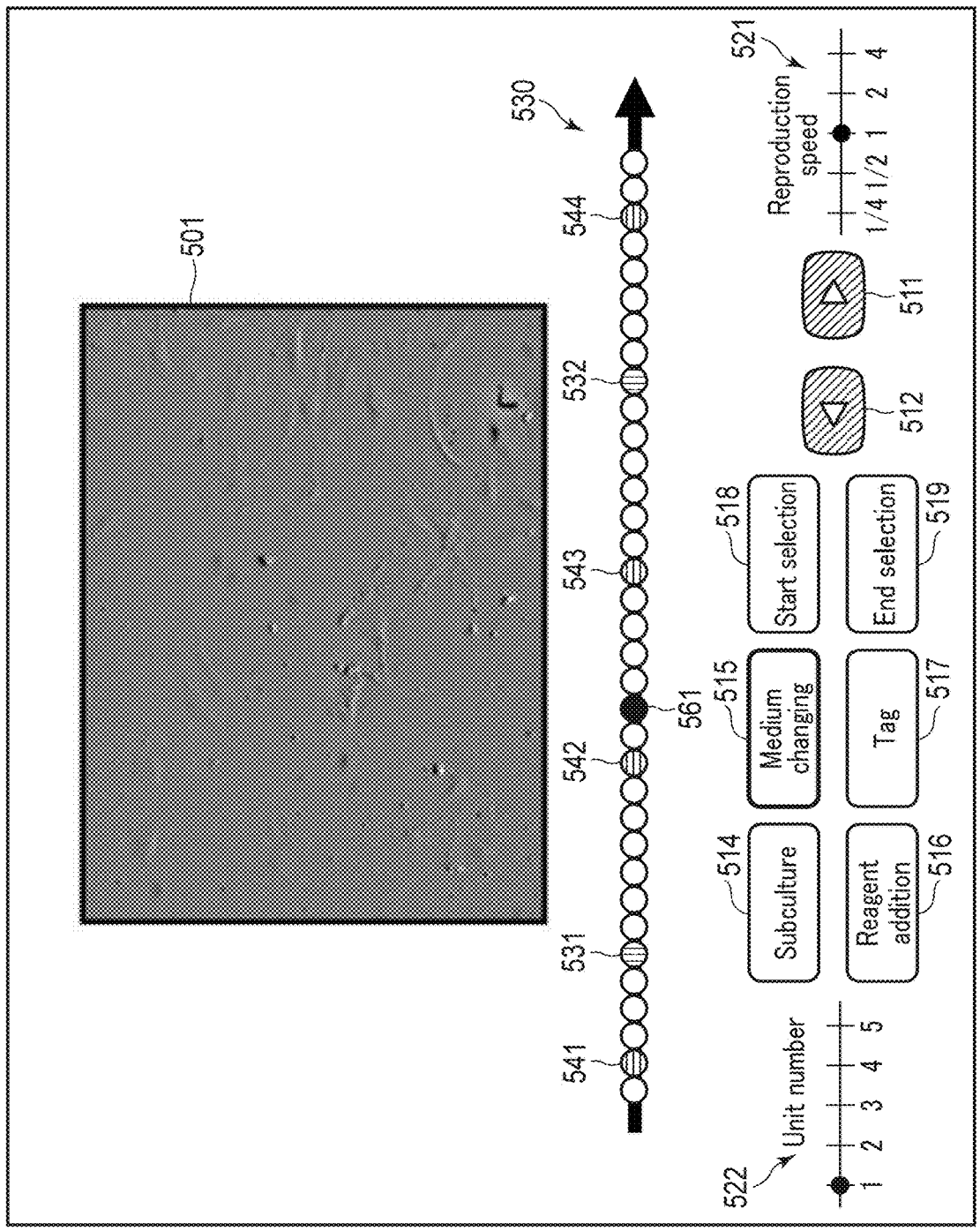
F I G. 6A

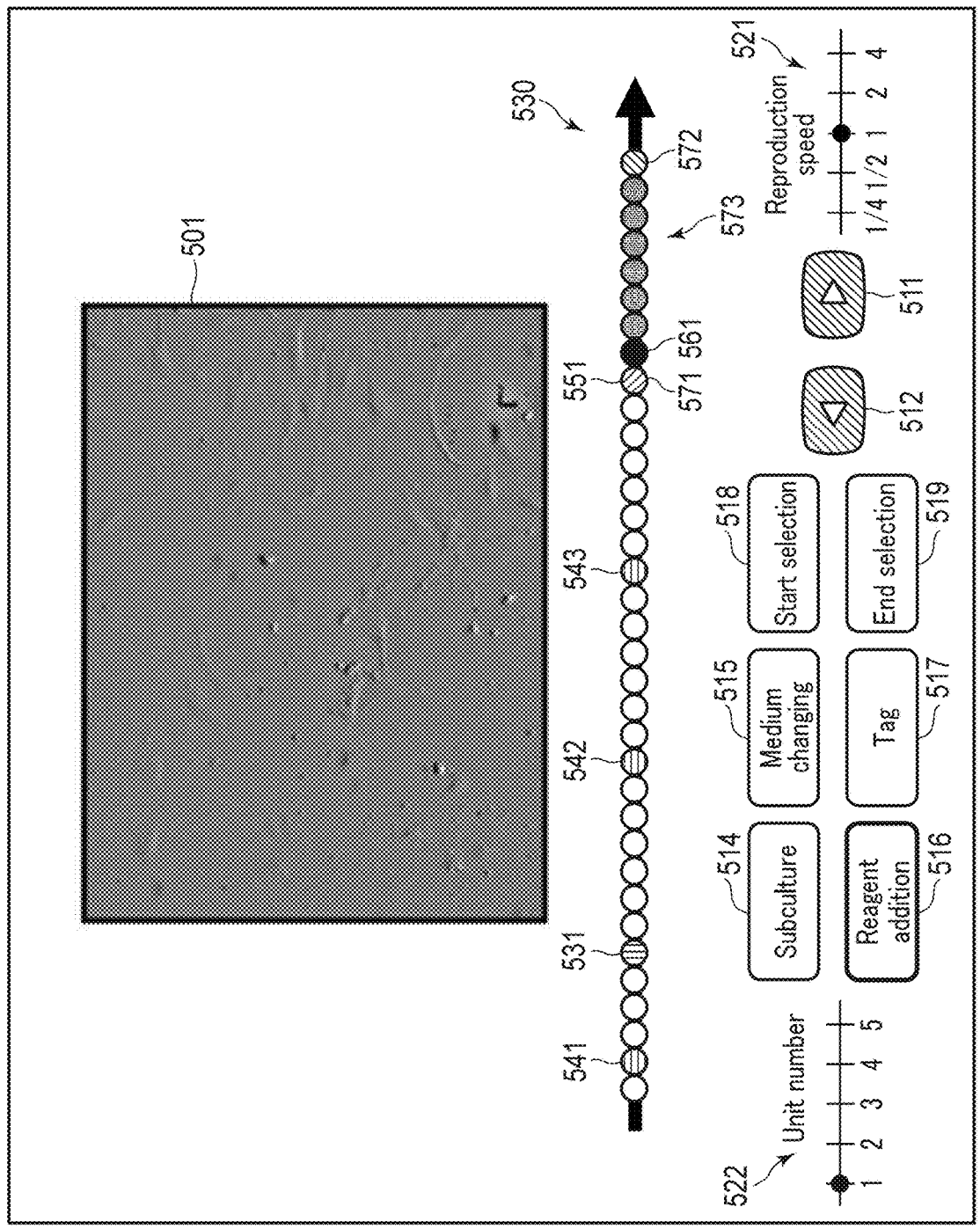
F I G. 7B

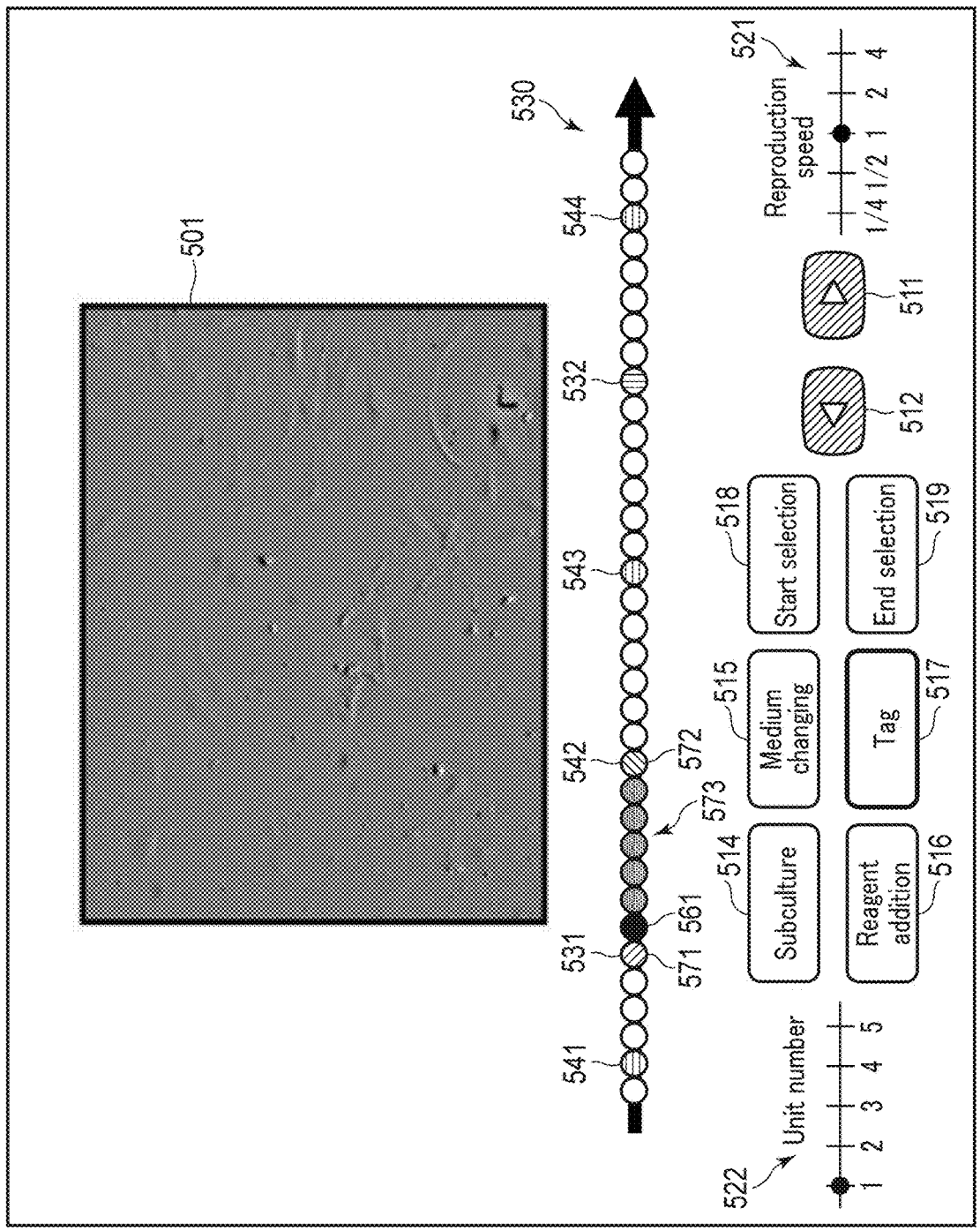
F I G. 8B

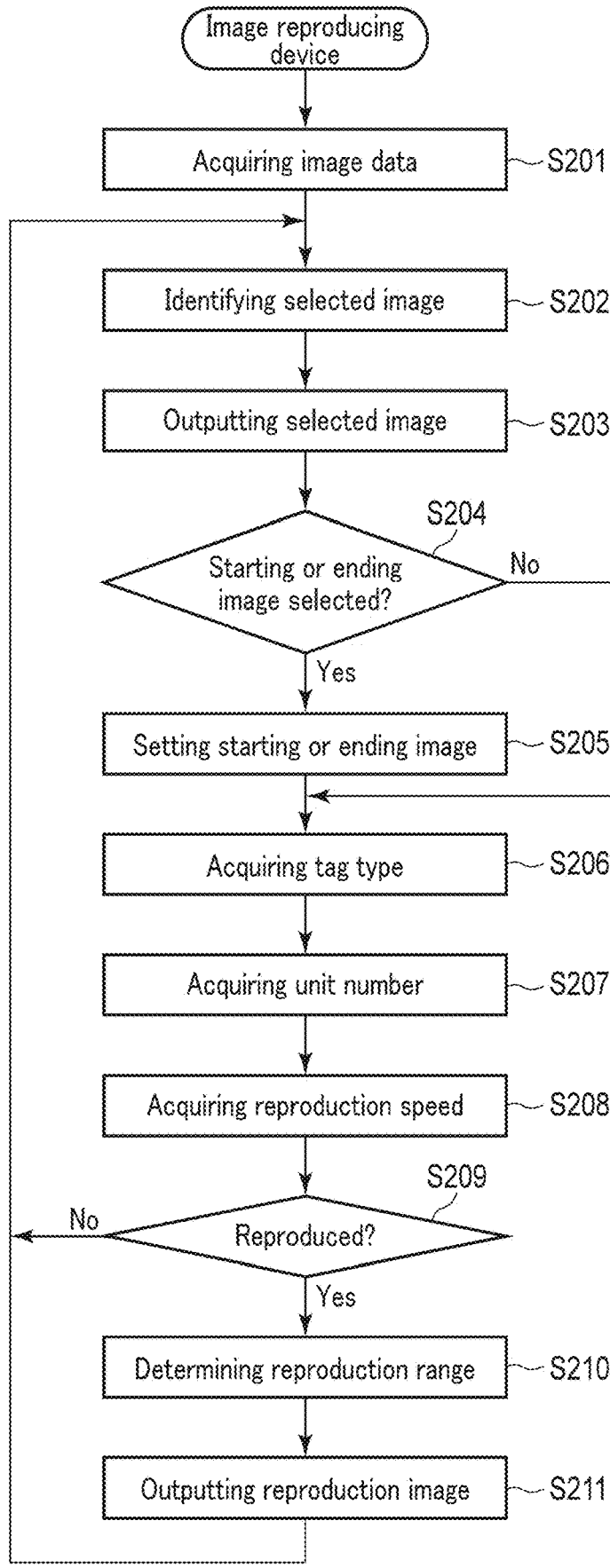
F I G. 12

IMAGE REPRODUCING DEVICE AND OBSERVATION SYSTEM FOR SELECTING IMAGES USING TAG INFORMATION ATTACHED IN ACCORDANCE WITH INFORMATION THAT OPERATION IS PERFORMED ON SAMPLE AND INPUT WHEN AT LEAST ONE OF IMAGES IS ACQUIRED

CROSS-REFERENCE TO RELATED APPLICATIONS

This application is a Continuation Application of PCT Application No. PCT/JP2017/017583, filed May 9, 2017, the entire contents of which are incorporated herein by reference.

FIELD

The embodiments relate to an image reproducing device and an observation system.

BACKGROUND

Cell culture is routinely performed in, for example, biotechnological researches, etc. In cell culture, checking a state of cells requires periodic operations to take out a culture container from an incubator and observe cells using a microscope, etc. Such an operation for checking is burdensome to an operator. For example, Jpn. Pat. Appln. KOKAI Publication No. 2002-85054 discloses a culture observation system that enables a state of cells in an incubator to be remotely observed so that the burden of such a burdensome operation can be reduced.

Cell culture is performed over a long period. Thus, imaging a state of cells in an incubator results in the accumulation of a large amount of image data along time series even at intervals.

SUMMARY

According to an aspect, an image reproducing device includes one or more processors. The processor acquires image group data including a plurality of images and tag information on at least one tag. The images relate to a biological sample along time series. The tag information relates to an operation on the biological sample and is associated with at least part of the images. The processor selects from the plurality of images using the tag information, images to be reproduced along the time series as reproduction selected images. The processor outputs to a display, data relating to the images for the reproduction selected images to be reproduced along time series.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 2 is a block diagram illustrating an outline of the configuration example of the observation system according to the embodiment.

FIG. 4A is a view illustrating an outline of an example of a display screen according to the embodiment.

FIG. 5B is a view illustrating an outline of an example of the display screen according to the embodiment.

FIG. 6A is a view illustrating an outline of an example of the display screen according to the embodiment.

FIG. 7B is a view illustrating an outline of an example of the display screen according to the embodiment.

FIG. 8B is a view illustrating an outline of an example of the display screen according to the embodiment.

FIG. 12 is a flowchart illustrating an outline of an example of an operation of the observation apparatus according to the embodiment.

DETAILED DESCRIPTION

[Configuration of Observation System]

Figure 1:
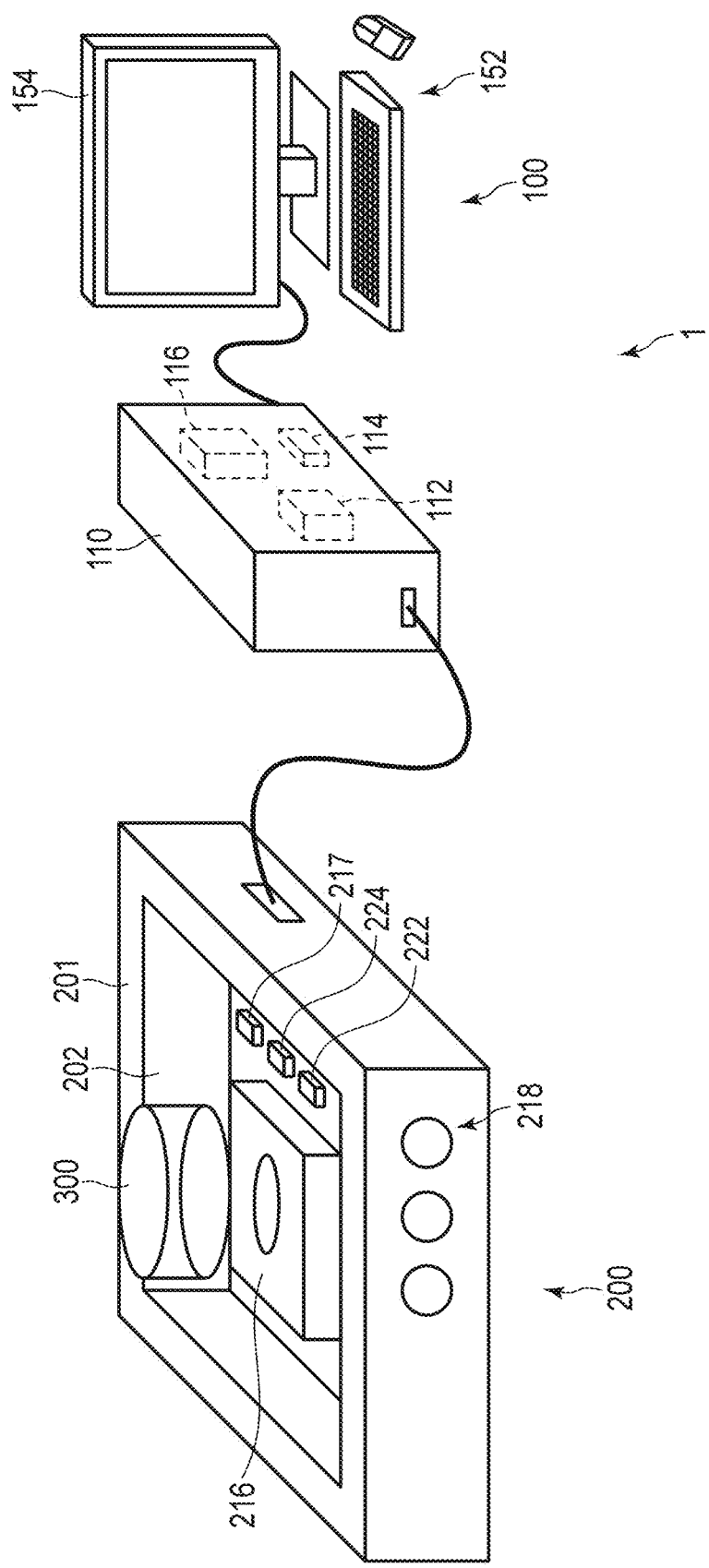
FIG. 1 is an external view illustrating an outline of a configuration example of an observation system according to an embodiment.

An embodiment will be described with reference to the drawings. The present embodiment relates to an observation system 1. The observation system 1 acquires images relating to a biological sample such as a cultured cell along time series. Furthermore, the observation system 1 reproduces the acquired images. Therefore, the observation system 1 includes an observation apparatus 200 that acquires images relating to a biological sample and a control apparatus 100 as an image reproducing device that reproduces the acquired images, as shown in FIG. 1, for example.

An observation object of the observation system 1 is a sample 300. The sample 300 includes a biological sample such as cultured cells, etc. Cultured cells, etc., are cultured in a medium placed in a petri dish, a flask, a multiwell dish, etc. The observation apparatus 200 is disposed inside an incubator, and the sample 300 is statically placed on the observation apparatus 200 inside the incubator. The observation apparatus 200 is capable of continuously acquiring images of cultured cells, etc., being cultured in the incubator. The control apparatus 100 connected to the observation apparatus 200 is disposed outside the incubator.

The observation apparatus 200 has an appearance in a substantially rectangular parallelepiped shape, for example. A transparent plate 202 is provided on the upper surface of a housing 201 of the observation apparatus 200. A sample as an observation object is disposed on the transparent plate 202. An imaging unit 216 including an imaging optical system and an imaging element is provided inside the housing 201. The imaging unit 216 images the sample 300 through the transparent plate 202 to generate image data of the sample 300. The generated image data is recorded in a recording device (not shown) inside the observation apparatus 200 or transmitted to the control apparatus 100. The imaging unit 216 may be fixed to image one part of the sample 300, or may be movable to image a plurality of parts of the sample 300.

The observation apparatus 200 includes an input interface 218 including button switches, for example. In order for a user to record an operation performed by himself or herself, for example, when changing a medium of the sample 300, the user presses one of button switches of the input interface 218, and for example, when performing an operation to subculture the sample 300, the user presses another button switch of the input interface 218. When performing a different operation such as addition of a reagent to the sample 300, the user presses yet another button switch. Records of, e.g., medium changing and a subculture operation of the sample 300, input via the input interface 218, are recorded in the recording device 217 of the observation apparatus 200 in such a manner that the records are associated with the image data generated by the imaging unit 216.

The observation apparatus 200 includes a processor 222 such as a central processing unit (CPU), an application specific integrated circuit (ASIC), a field programmable gate array (FPGA), etc. There is no limit on the number of processors 222. The observation apparatus 200 includes a memory 224 that functions as a main memory of the processor 222, and a recording device 217 that records various types of information. The memory 224 is, for example, a random access memory (RAM). The recording device 217 may be, for example, a semiconductor memory, a hard disk, etc. The recording device 217 records programs for use in the processor 222, various parameters, etc. The recording device 217 records the acquired image data relating to the sample 300, etc.

The control apparatus 100 includes an image reproducing device 110, an input interface 152, and a display 154. The image reproducing device 110 may be, for example, a personal computer (PC), a tablet terminal, etc. The input interface 152 may be, for example, a keyboard, a mouse, a touch panel, etc. The display 154 may be, for example, a liquid crystal display, etc.

The image reproducing device 110 causes the display 154 to display an image acquired by the observation apparatus 200. The image reproducing device 110 may control the observation apparatus 200. The image reproducing device 110 includes a processor 112 such as a central processing unit (CPU), an application specific integrated circuit (ASIC), a field programmable gate array (FPGA), a graphics processing unit (GPU), etc. There is no limit on the number of processors 112. The image reproducing device 110 includes a memory 114 that functions as a main memory of the processor 112, and a recording device 116 that records various types of information. The memory 114 is, for example, a random access memory (RAM), etc. The recording device 116 may be, for example, a semiconductor memory, a hard disk, etc. The recording device 116 records programs for use in the processor 112, various parameters, etc. The recording device 116 records, e.g., image data that relates to the sample 300 and is acquired from the observation apparatus 200.

The function of the observation system 1 will be described with reference to the block diagram shown in FIG. 2. The observation apparatus 200 includes an imaging controller 211 and a recording controller 212 in addition to the imaging unit 216, the recording device 217, and the input interface 218 described above. The imaging controller 211 and the recording controller 212 may be realized by the processor 222, etc. The imaging controller 211 controls the operation of the imaging unit 216. The recording controller 212 controls recording of the image data obtained by the imaging unit 216, in the recording device 217.

The image reproducing device 110 includes a data acquisition unit 122, an input information acquisition unit 124, a reproduced image selection unit 126, and a reproduced image outputting unit 128. The data acquisition unit 122 acquires image group data including a plurality of images along time series relating to the sample 300 as a biological sample, and tag information on at least one tag relating to an operation on the sample 300, associated with at least part of the images. The input information acquisition unit 124 acquires information input to the input interface 152. The input to the input interface 152 is used to reproduce images. The reproduced image selection unit 126 selects from a plurality of images using the tag information, images to be reproduced along time series as reproduction selected images. The reproduced image outputting unit 128 outputs to the display 154, data relating to images for reproducing the reproduction selected images along time series.

[Operation Outline of Observation System]

The observation system 1 according to the present embodiment acquires a plurality of images of the sample 300 along time series and performs continuous observation. That is, the observation apparatus 200 images using the imaging unit 216 the sample 300 statically placed on the transparent plate 202, for example, at predetermined time intervals, to acquire data of a plurality images. Such imaging is repeated, for example, every hour, and is continued for, for example, several weeks. Therefore, the number of images obtained by imaging may reach several hundred.

Imaging is performed for, for example, several weeks. Thus, a medium of the sample 300 may be changed, or a subculture operation, etc., may be performed on the cells, etc., of the sample 300. In such observation, a reagent may be added to the sample 300 in the middle of observation, and the effect of the added reagent may be evaluated. In the present embodiment, when performing an operation such as a medium changing operation, a subculture operation, a reagent adding operation, etc., a user inputs this fact to the observation apparatus 200 using the input interface 218. The observation apparatus 200 records information relating to the operation input thereto in a manner such that the information is associated with the acquired images.

Figure 3:
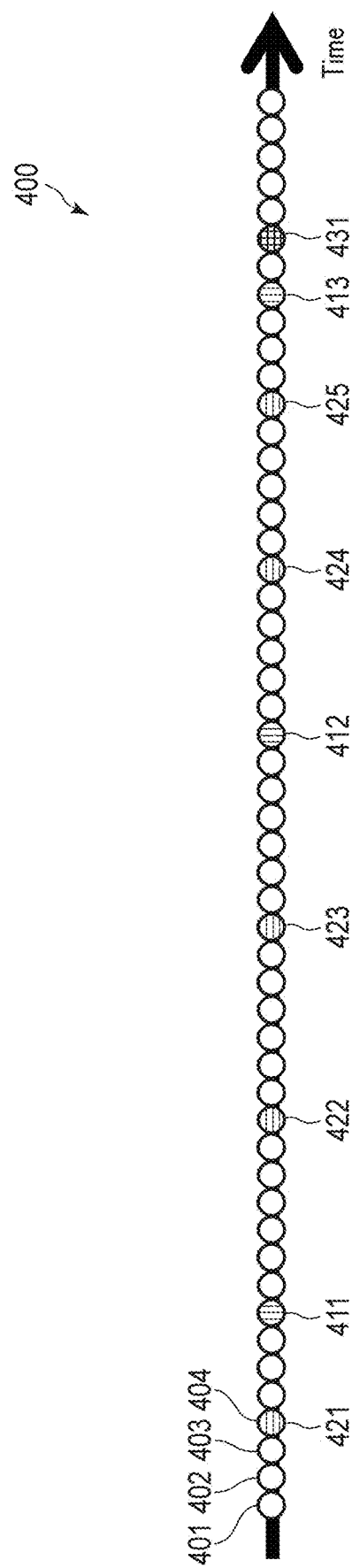
FIG. 3 is a view schematically illustrating a configuration example of image group data according to the embodiment.

A configuration example of data obtained by the observation system 1 will be described with reference to FIG. 3. FIG. 3 is a view schematically showing image group data 400 including a plurality of images obtained by the observation system 1 and information relating to an operation. In FIG. 3, one circle schematically represents one image. For example, the image group data 400 includes data relating to a plurality of images along time series, such as a first image 401, a second image 402, a third image 403, a fourth image 404, etc.

The observation apparatus 200 receives input of the fact that a subculture operation has been performed by a user. Based on this input, the observation apparatus 200 attaches a tag indicative of the fact that a subculture operation has been performed, to the image obtained by the first imaging after the subculture operation. For example, in FIG. 3, a circle with hatching of vertical lines indicates an image to which a subculture operation tag is attached. For example, this image to which a subculture operation tag is attached corresponds to a first subculture operation tagged image 411, a second subculture operation tagged image 412, a third subculture operation tagged image 413, etc.

The observation apparatus 200 receives input of the fact that medium changing has been performed by a user. Based on this input, the observation apparatus 200 attaches a tag indicative of the fact that medium changing has been performed, to the image obtained by the first imaging after the medium changing. For example, in FIG. 3, a circle with hatching of horizontal lines indicates an image to which a medium changing tag is attached. For example, this image to which a medium changing tag is attached corresponds to a first medium changing tagged image 421 serving as the fourth image 404. Moreover, the image to which a medium changing tag is attached corresponds to a second medium changing tagged image 422, a third medium changing tagged image 423, a fourth medium changing tagged image 424, a fifth medium changing tagged image 425, etc.

The observation apparatus 200 receives input of the fact that a different operation has been performed by a user. Herein, examples of a different operation may include addition of a predetermined reagent to the sample 300. Based on this input, the observation apparatus 200 attaches a tag indicative of the fact that a different operation has been performed to the image obtained by the first imaging after the aforementioned different operation. For example, in FIG. 3, a circle with lattice hatching indicates an image to which a reagent addition tag is attached. For example, this image to which a reagent addition tag is attached is a first reagent addition tagged image 431, etc. As described above, various operation tags may be attached to images.

The image group data 400 such as shown in FIG. 3 is recorded in the recording device 217 of the observation apparatus 200. The data acquisition unit 122 of the image reproducing device 110 acquires the image group data 400 from the recording device 217 of the observation apparatus 200. The input information acquisition unit 124 of the image reproducing device 110 acquires a user's input from the input interface 152. Based on the user's input acquired by the input information acquisition unit 124, the reproduced image selection unit 126 selects an image to be reproduced from images included in the image group data 400 acquired by the data acquisition unit 122. For example, the reproduced image selection unit 126 selects as reproduction selected images, a series of images desired by a user, which are part of many images included in the image group data 400. The reproduced image outputting unit 128 outputs to the display 154, image data including the images selected by the reproduced image selection unit 126 as reproduction data, and causes the display 154 to display these images, etc. For example, the display 154 displays a time-lapse movie image in which a plurality of images included between specific operations are continuously displayed. A display form of reproduction selected images is not limited to a time-lapse movie image. Reproduction selection images may take any display form such as display of a list, display in which images are switched according to a user's instruction, and so on.

[Outline of Image Reproduction Operation]

A reproduction image selected by the reproduced image selection unit 126 of the image reproducing device 110 will be described. FIG. 4A shows an example of a reproduction screen 500 displayed on the display 154. Herein, FIG. 4A shows a screen for a user to select, for example, an image of interest to him or her before reproduction of a time-lapse movie image, and to input the selected image to the image reproducing device 110.

As shown in FIG. 4A, the reproduction screen 500 includes an image display area 501. The image display area 501 displays an image included in the image group data 400. The reproduction screen 500 includes a time bar 530. The time bar 530 schematically shows images included in the image group data 400. The time bar 530 shows a temporal relationship between images obtained over time. In the time bar 530, respective images may be indicated by symbols such as circles in FIG. 4A, scale marks assigned to the bar, or thumbnail images arranged in a line. The time bar 530 may display part or all of images included in the image group data 400. When the time bar 530 displays part of images included in the image group data 400, the images displayed on the time bar 530 are changeable by a predetermined operation.

The time bar 530 explicitly shows images to which a subculture operation tag is attached, such as the first subculture operation tagged image 531 and the second subculture operation tagged image 532 indicated with vertical hatching in the example shown in FIG. 4A. The time bar 530 explicitly shows images to which a medium changing tag is attached, such as a first medium changing tagged image 541, a second medium changing tagged image 542, a third medium changing tagged image 543, a fourth medium changing tagged image 544 indicated with horizontal hatching in the example shown in FIG. 4A. Similarly, the time bar 530 explicitly shows an image to which a reagent addition tag is attached.

The time bar 530 explicitly shows an image currently selected by a user, such as a selected image 561 indicated by a black circle in the example shown in FIG. 4A. For example, a user selects a desired image from images shown on the time bar 530 by, for example, moving a cursor using a mouse and clicking while pointing to a desired image on the time bar 530. The time bar 530 explicitly shows the image selected by a user. The selected image is displayed as a still image in the image display area 501.

The reproduction screen 500 includes a reproduction icon 511 and a reverse reproduction icon 512. When the reproduction icon 511 is clicked, for example, images to be reproduced are selected based on the selected image 561, etc., and the images selected in this way are displayed in the image display area 501 as a time-lapse movie image in time order. When the reverse reproduction icon 512 is clicked, for example, images to be reproduced are selected based on the selected image 561, etc., and the images selected in this way are displayed in the image display area 501 as a time-lapse movie image in reverse order of time.

The aforementioned images to be reproduced may be all of images included in the image group data, or may be a predetermined image selected from a plurality of images included in the image group data, as described in detail herein.

The reproduction screen 500 includes a reproduction speed adjustment display 521. The reproduction speed adjustment display 521 is configured in a manner to allow a reproduction speed to be selected, for example. By using the reproduction speed adjustment display 521, a user can input a desired reproduction speed of a time-lapse movie image to the image reproducing device 110. The image reproducing device 110 operates in a manner such that a time-lapse movie image that is reproduced by the reproduction icon 511 or the reverse reproduction icon 512 being clicked; and for example, its reproduction speed is equal to the speed selected using the reproduction speed adjustment display 521.

The reproduction screen 500 includes a subculture icon 514, a medium changing icon 515, a reagent addition icon 516, a tag icon 517, a start selection icon 518, an end selection icon 519, and a unit number adjustment display 522. The reproduced image selection unit 126 selects an image to be reproduced, in accordance with user's operation using those icons.

Figure 4B:
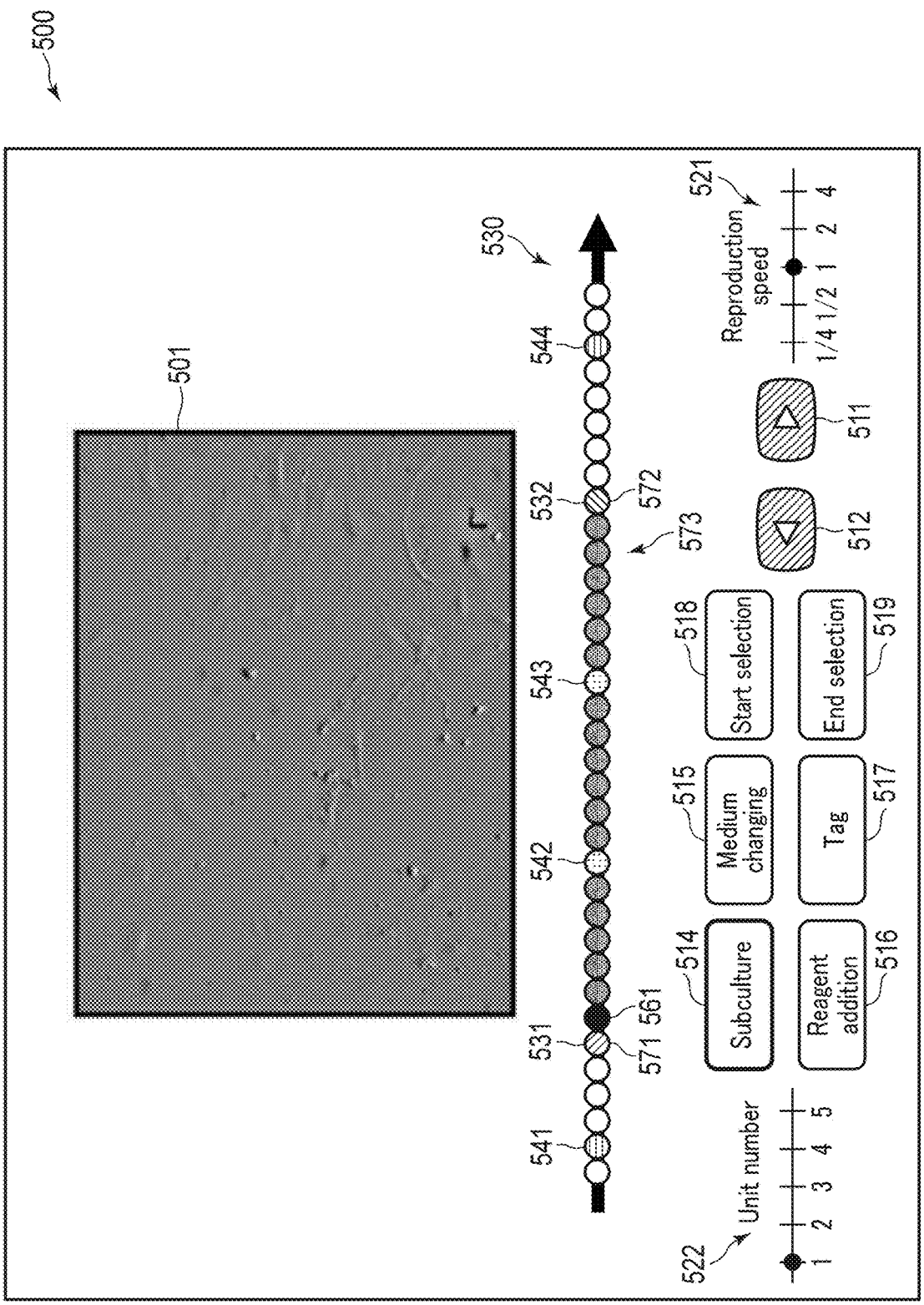
FIG. 4B is a view illustrating an outline of an example of the display screen according to the embodiment.

For example, in the example shown in FIG. 4A, the subculture icon 514 is selected. If the reproduction icon 511 is selected in this state, a plurality of images ranging from the first image to the last image are selected as the reproduction selected images 573. Herein, the first image is the first subculture operation tagged image 531 as an image which the subculture operation tag is attached to and is obtained immediately before the selected image 561. The last image is the second subculture operation tagged image 532 as an image which the subculture operation tag is attached to and is obtained immediately after the selected image 561. That is, as shown in FIG. 4B, the first subculture operation tagged image 531 with diagonal hatching slanting downward to the right is set as a starting image 571, while the second subculture operation tagged image 532 with diagonal hatching slanting upward to the right is set as an ending image 572. In this manner, the shaded images ranging from the starting image 571 to the ending image 572 are selected as the reproduction selected images 573. At this time, the images ranging from the starting image 571 to the ending image 572 are sequentially displayed in the image display area 501 as a time-lapse movie image.

Figure 4C:
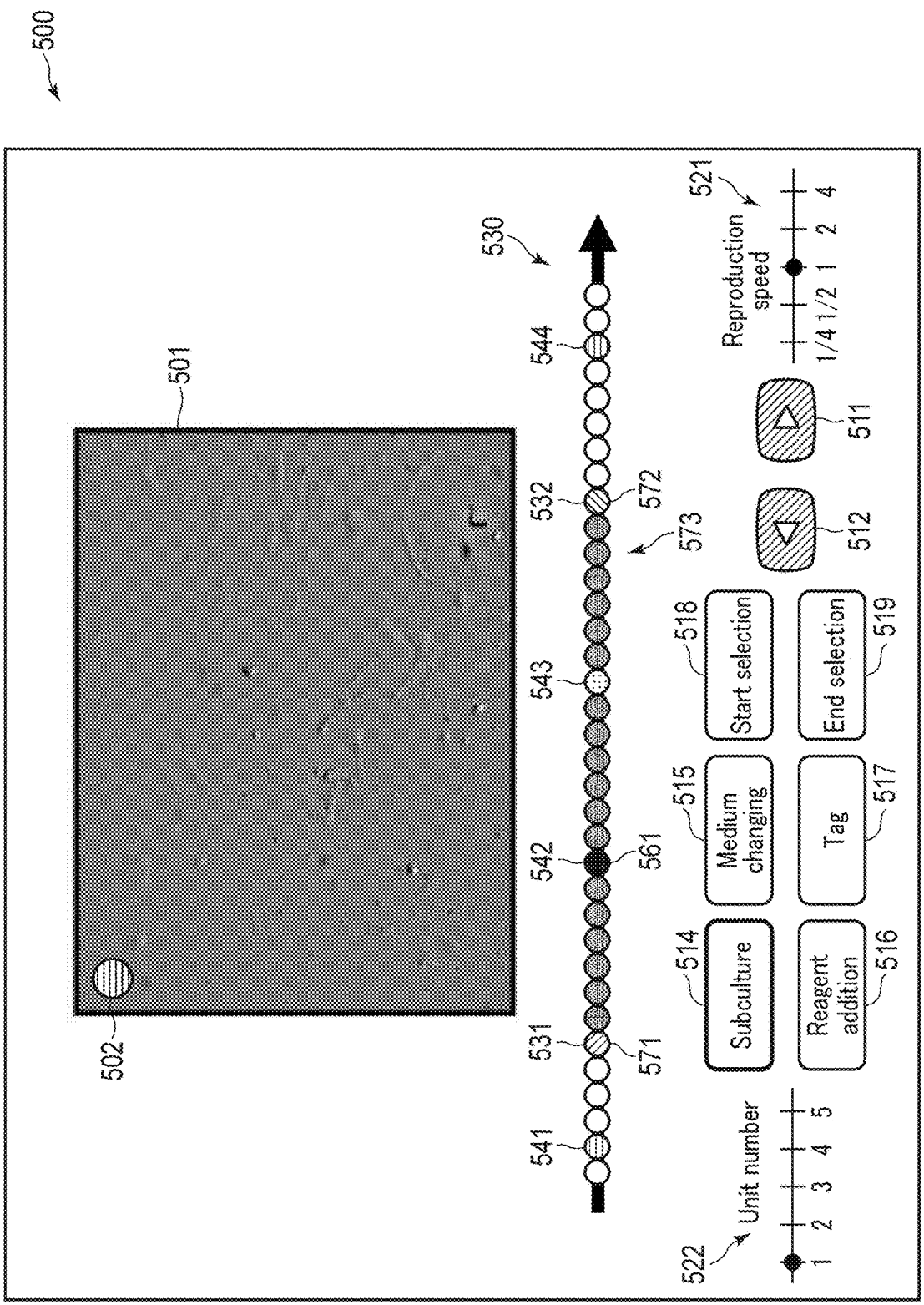
FIG. 4C is a view illustrating an outline of an example of the display screen according to the embodiment.

When the images are being reproduced as a time-lapse movie image, the display of the selected image 561 on the time bar 530 indicates an image being displayed in the image display area 501. If the image displayed in the image display area 501 is a tagged image, this fact may be displayed as tag information 502 inside the image display area 501, for example, as shown in FIG. 4C.

Figure 5A:
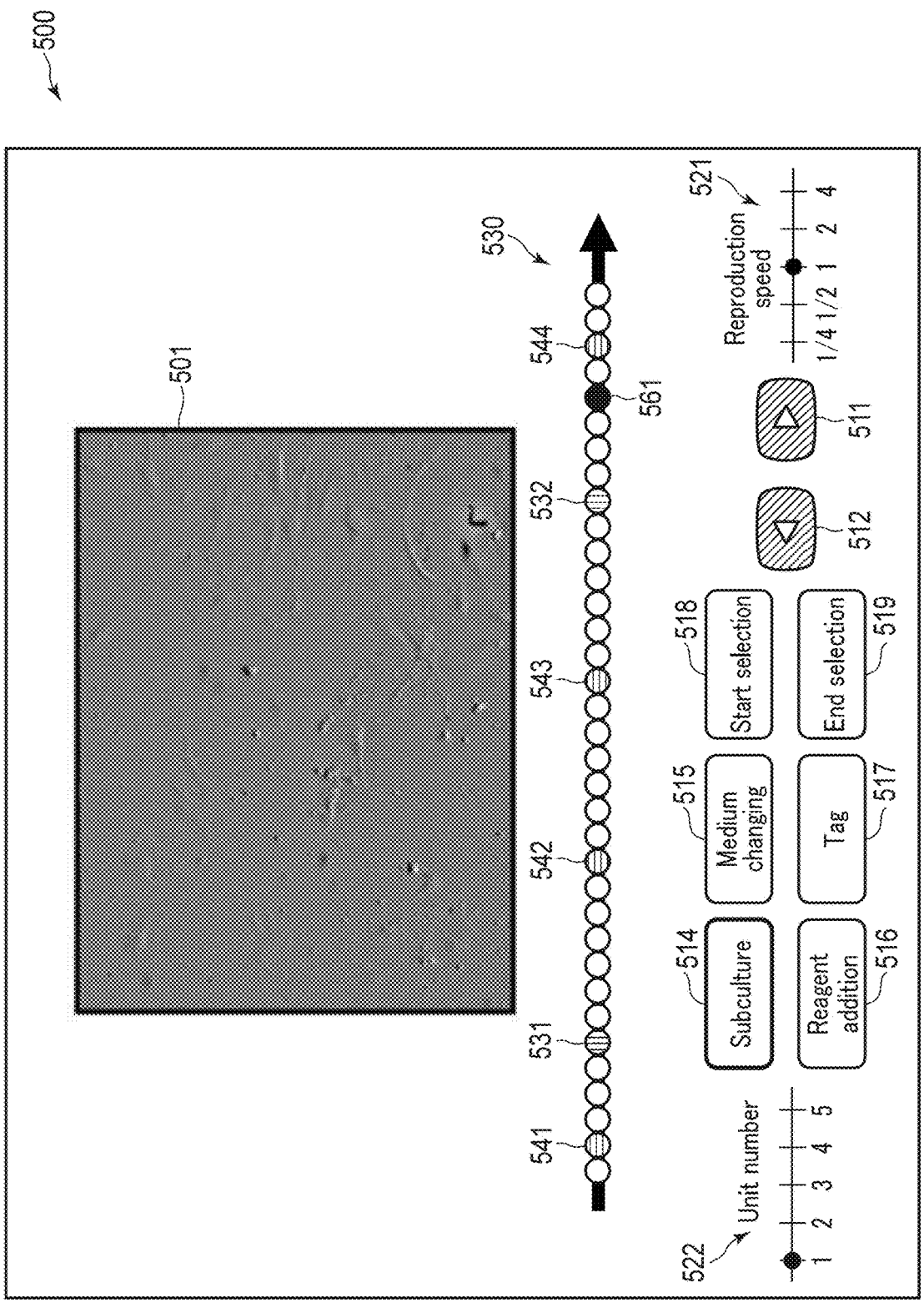
FIG. 5A is a view illustrating an outline of an example of the display screen according to the embodiment.

FIG. 5A shows a state in which the subculture icon 514 is selected while a subculture operation tagged image exists only before the selected image 561, not after the selected image 561. Assume that the reproduction icon 511 is selected in this state. In such a case, as shown in FIG. 5B, the starting image 571 is set as the second subculture operation tagged image 532 as an image which the subculture operation tag is attached to and is obtained immediately before the selected image 561, while the ending image 572 is set as the latest image, that is, an image obtained by the last imaging. As a result, the shaded images ranging from the starting image 571 as the second subculture operation tagged image 532 to the ending image 572 as the latest image are selected as the reproduction selected images 573, and these selected images are displayed in the image display area 501 as a time-lapse movie image. Generally, an image close to the present time tends to be of most interest. Thus, it is significant that the latest image is set as the ending image 572 in this manner.

Similarly, assume that the reproduction icon 511 is selected in a state in which the subculture icon 514 is selected while a subculture operation tagged image exists only after the selected image 561, not before the selected image 561. In such a case, the starting image 571 is set as the first image, and the ending image 572 is set as the image which the subculture operation tag is attached to and is obtained immediately after the selected image 561.

Figure 6B:
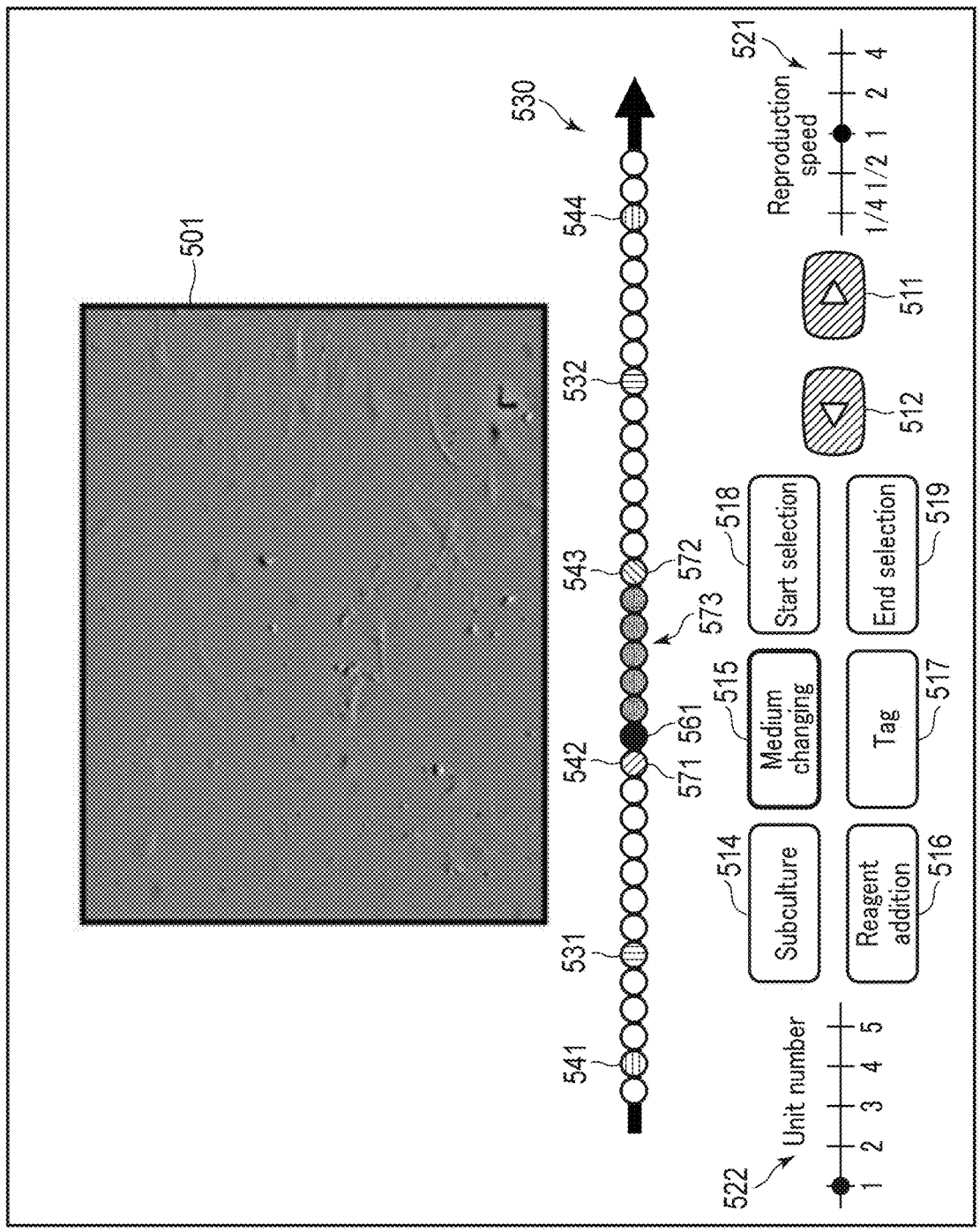
FIG. 6B is a view illustrating an outline of an example of the display screen according to the embodiment.

FIG. 6A shows an example in which the medium changing icon 515 is selected. If the reproduction icon 511 is selected in this state, images ranging from the second medium changing tagged image 542 to the third medium changing tagged image 543 are selected as the reproduction selected images 573. Herein, the second medium changing tagged image 542 is an image which the medium changing tag is attached to and is obtained immediately before the selected image 561. The third medium changing tagged image 543 is an image which the medium changing tag is attached to and is obtained immediately after the selected image 561. That is, as shown in FIG. 6B, the second medium changing tagged image 542 is set as the starting image 571, while the third medium changing tagged image 543 is set as the ending image 572. In this manner, the images ranging from the starting image 571 to the ending image 572 are selected as the reproduction selected images 573. At this time, the images ranging from the starting image 571 to the ending image 572 are sequentially displayed in the image display area 501 as a time-lapse movie image.

Figure 7A:
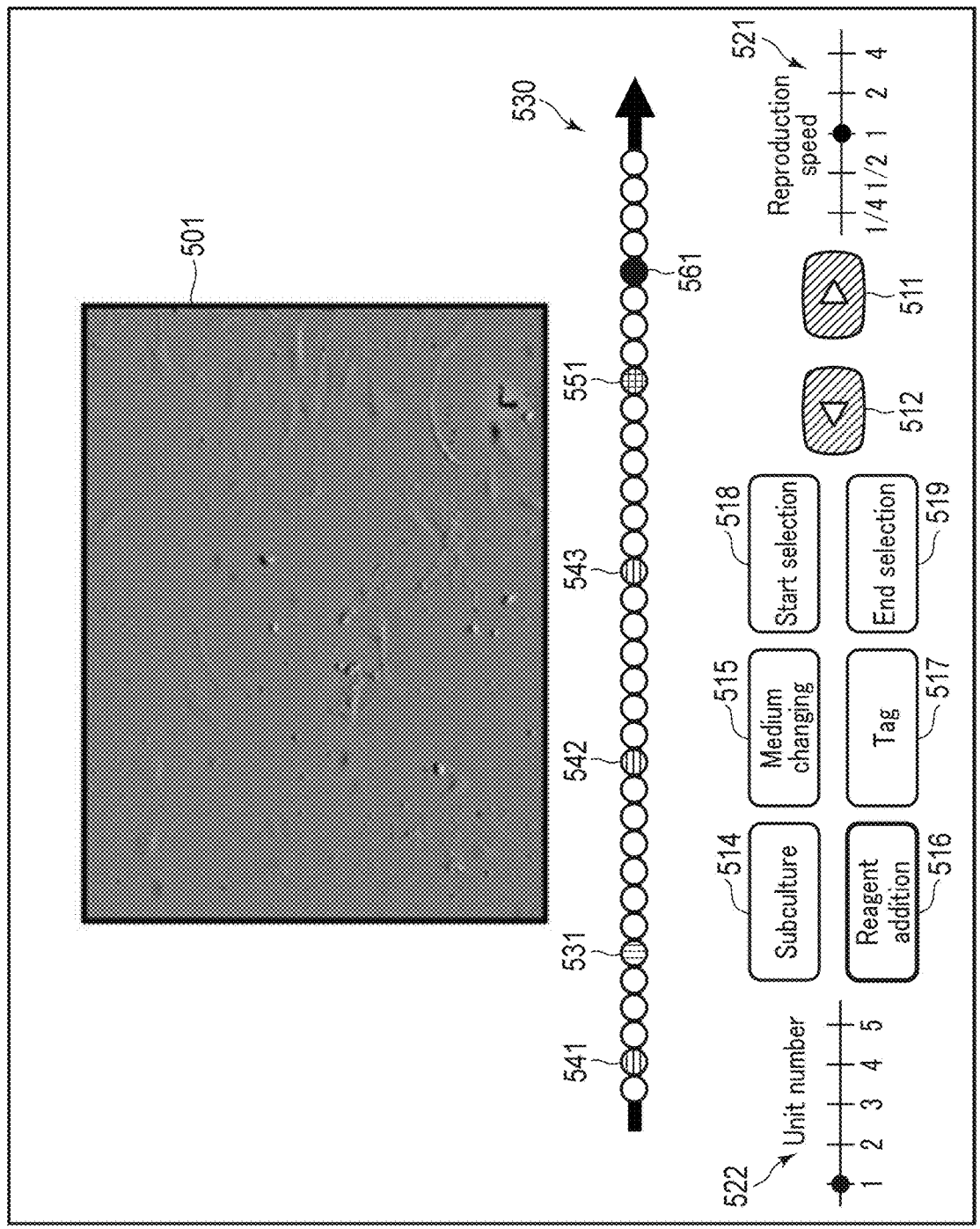
FIG. 7A is a view illustrating an outline of an example of the display screen according to the embodiment.

FIG. 7A shows an example in which the reagent addition icon 516 is selected. If the reproduction icon 511 is selected in this state, images ranging from the first reagent addition tagged image 551 as an image which the operation tag relating to reagent addition is attached to and is obtained immediately before the selected image 561, to an image which the operation tag relating to reagent addition is attached to and is obtained immediately after the selected image 561 are selected as the reproduction selected images 573. In the example shown in FIG. 7A, the ending image is set as the latest image since an image to which the operation tag relating to reagent addition is attached does not exist after the selected image 561. That is, as shown in FIG. 7B, the first reagent addition tagged image 551 is set as the starting image 571, while the latest image is set as the ending image 572. In this manner, the images ranging from the starting image 571 to the ending image 572 are selected as the reproduction selected images 573. At this time, the images ranging from the starting image 571 to the ending image 572 are sequentially displayed in the image display area 501 as a time-lapse movie image.

Figure 8A:
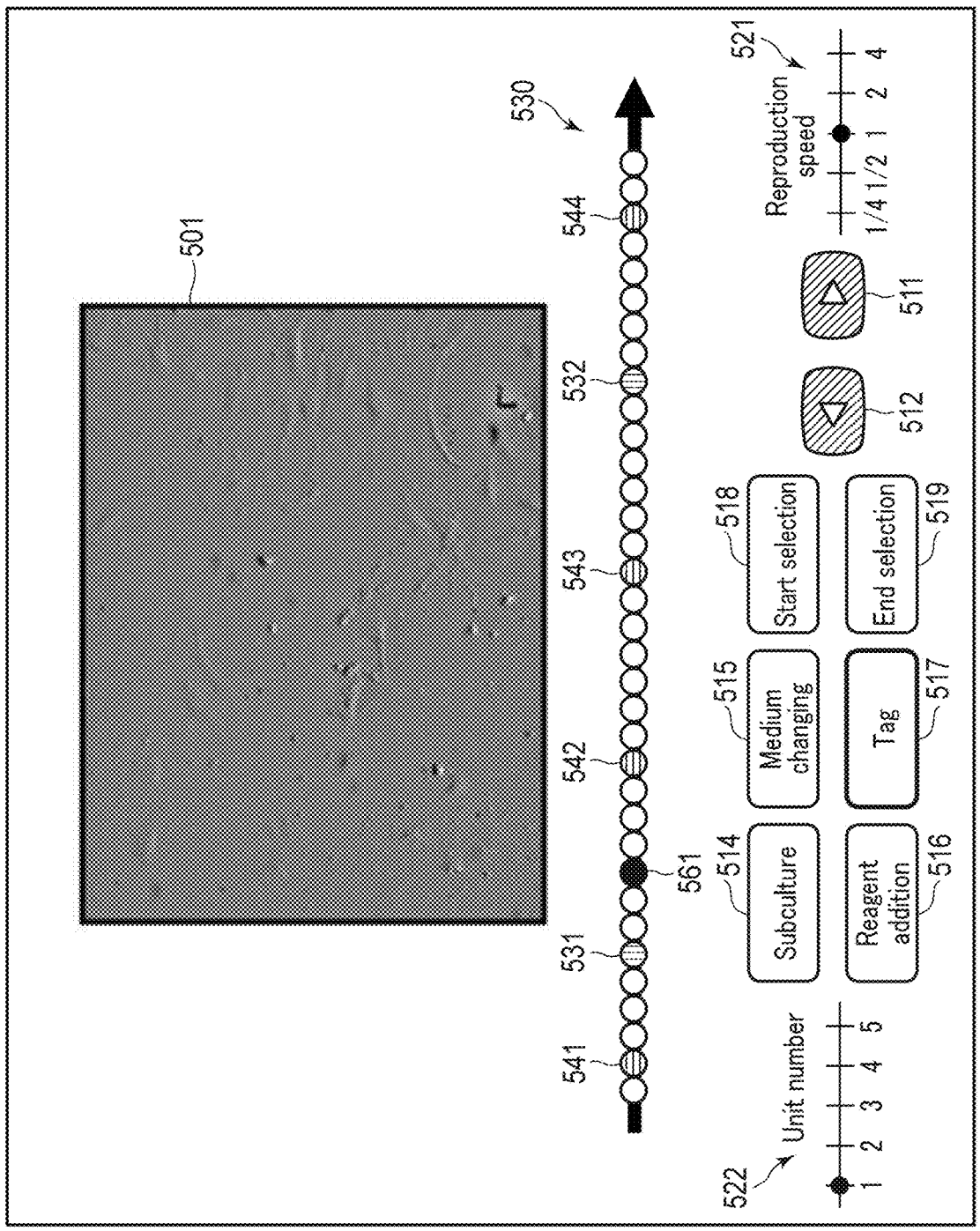
FIG. 8A is a view illustrating an outline of an example of the display screen according to the embodiment.

In the example shown in FIG. 8A, the tag icon 517 is selected. If the reproduction icon 511 is selected in this state, images ranging from the first subculture operation tagged image 531 as a tagged image obtained immediately before the selected image 561, to the second medium changing tagged image 542 as a tagged image obtained immediately after the selected image 561 are selected as the reproduction selected images 573. That is, as shown in FIG. 8B, the first subculture operation tagged image 531 is set as the starting image 571, while the second medium changing tagged image 542 is set as the ending image 572. In this manner, the images ranging from the starting image 571 to the ending image 572 are selected as the reproduction selected images 573. At this time, the images ranging from the starting image 571 to the ending image 572 are sequentially displayed in the image display area 501 as a time-lapse movie image.

Figure 9A:
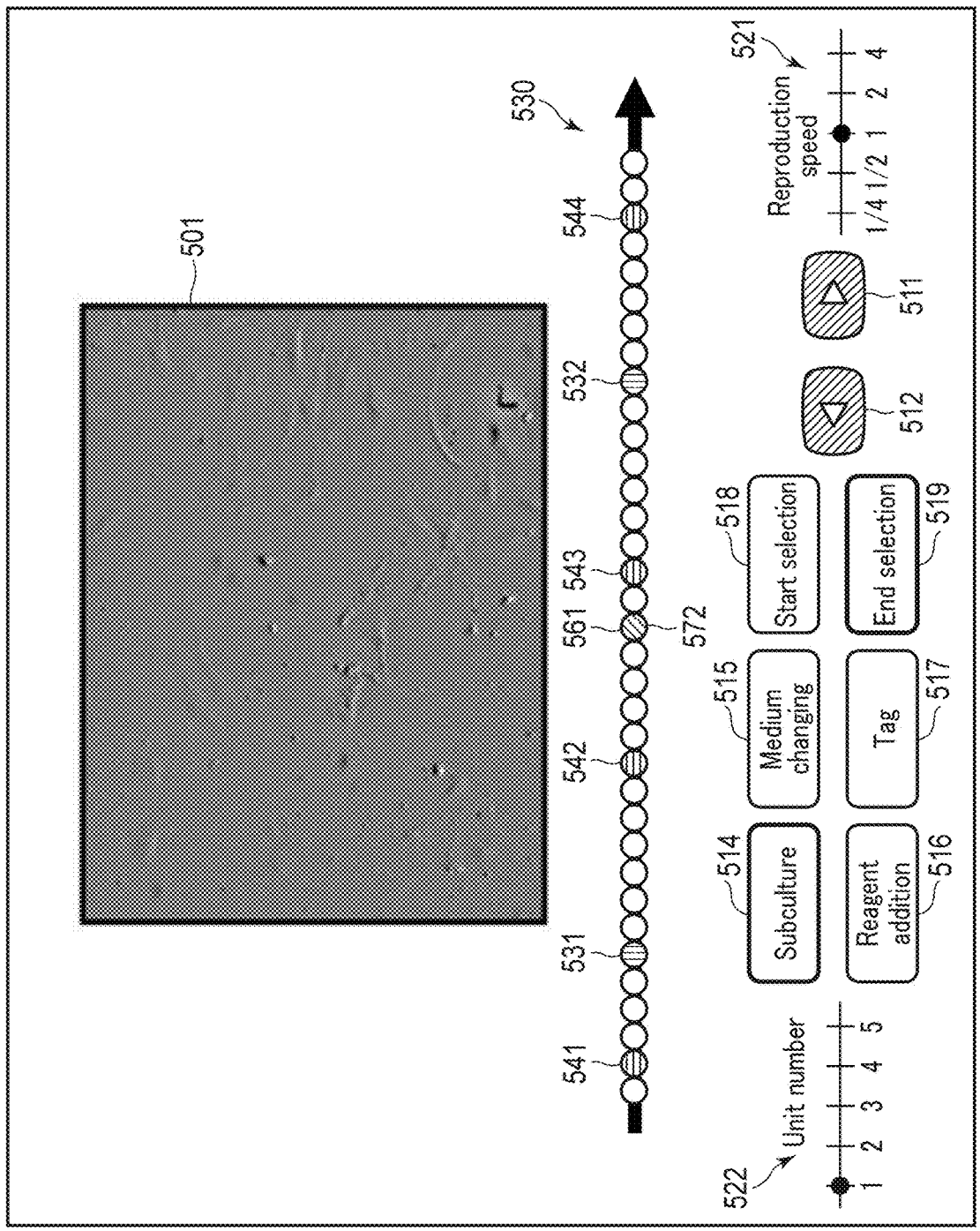
FIG. 9A is a view illustrating an outline of an example of the display screen according to the embodiment.
Figure 9B:
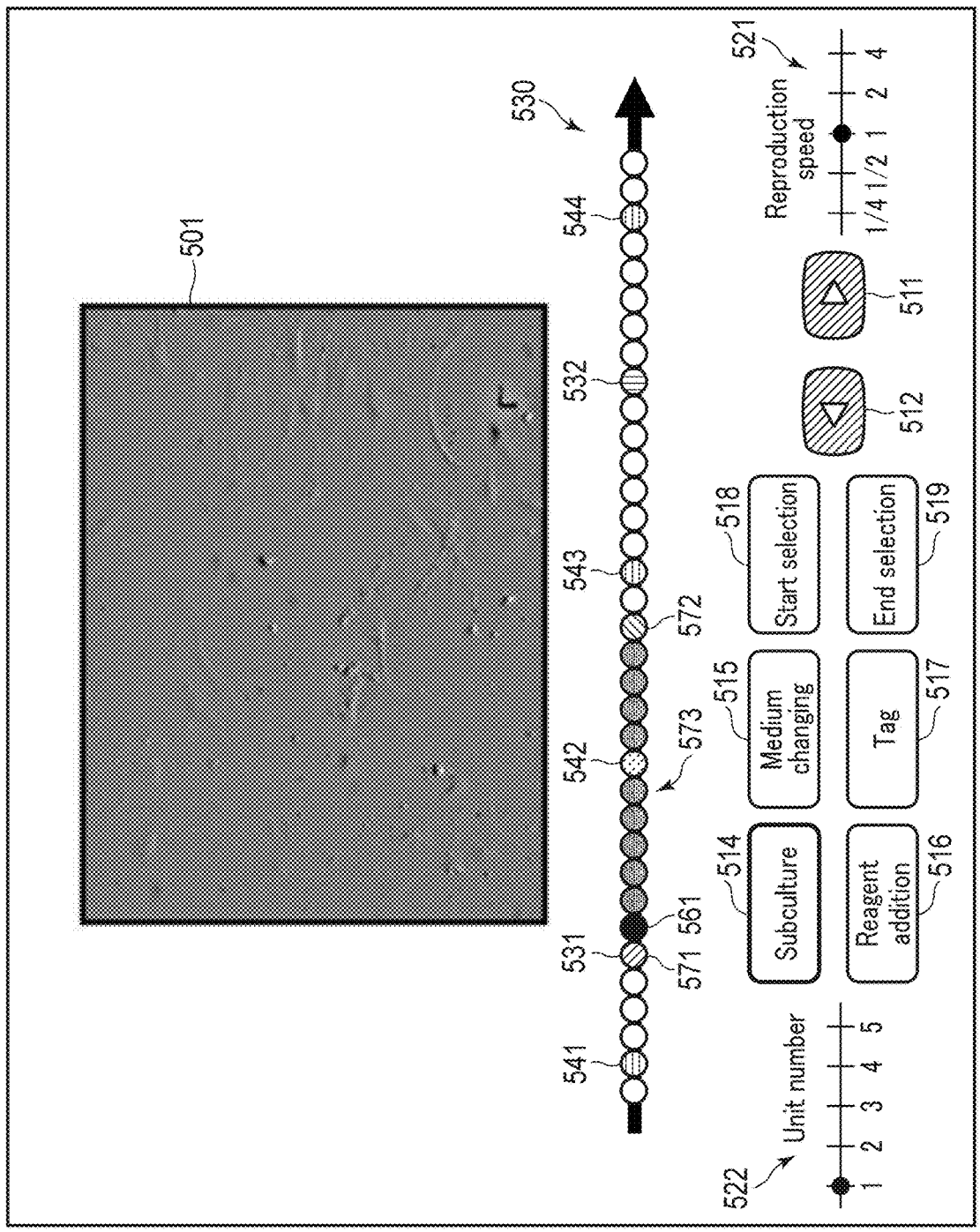
FIG. 9B is a view illustrating an outline of an example of the display screen according to the embodiment.

FIG. 9A shows an example in which the subculture icon 514 is selected. At this time, when the end selection icon 519 is selected in a state in which a single image is selected as the selected image 561, this selected image is set as the ending image 572 as shown in FIG. 9A. When the reproduction icon 511 is selected, as shown in FIG. 9B, the subculture operation tagged image 531 which the subculture operation tag is attached to and is obtained immediately before the selected image 561 is set as the starting image 571. As a result, the images ranging from the starting image 571 to the ending image 572 are sequentially displayed in the image display area 501 as a time-lapse movie image. Similarly, the starting image 571 may be designated by a user using the start selection icon 518. As described above, the starting image 571 or the ending image 572 may be selected by a user through direct designation. This improves user's freedom in selecting which image to reproduce.

The starting image 571 and the ending image 572 may be determined based on other rules. For example, an image that a user has not checked yet may be set as the starting image 571. In one example of such a case, the starting image 571 may be an image that is obtained for the first time after the image reproducing device 110 performs the last image display, for example, when images are reproduced while the observation apparatus 200 is continuously making the observation and then logout is performed in the image reproducing device 110.

Figure 10A:
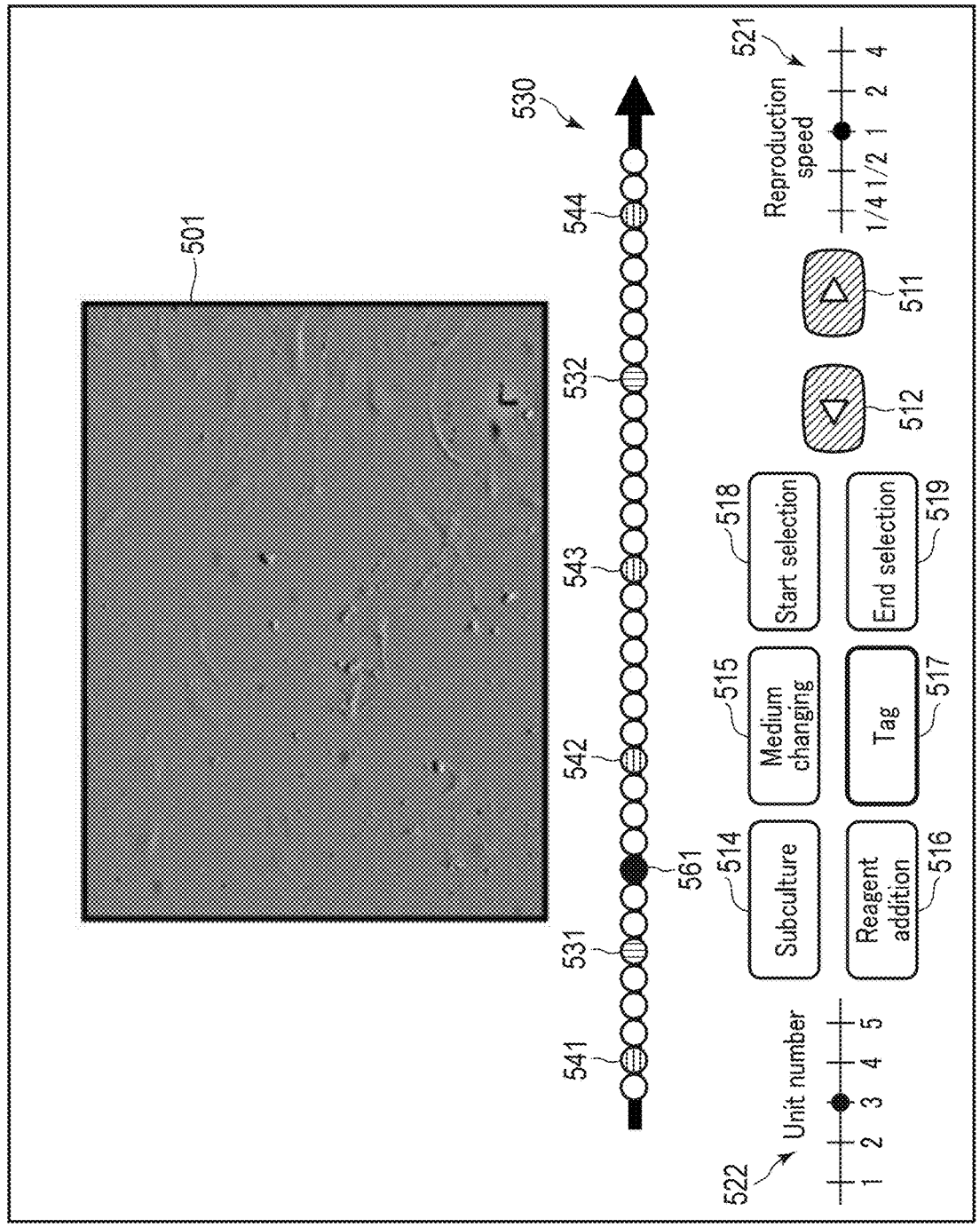
FIG. 10A is a view illustrating an outline of an example of the display screen according to the embodiment.
Figure 10B:
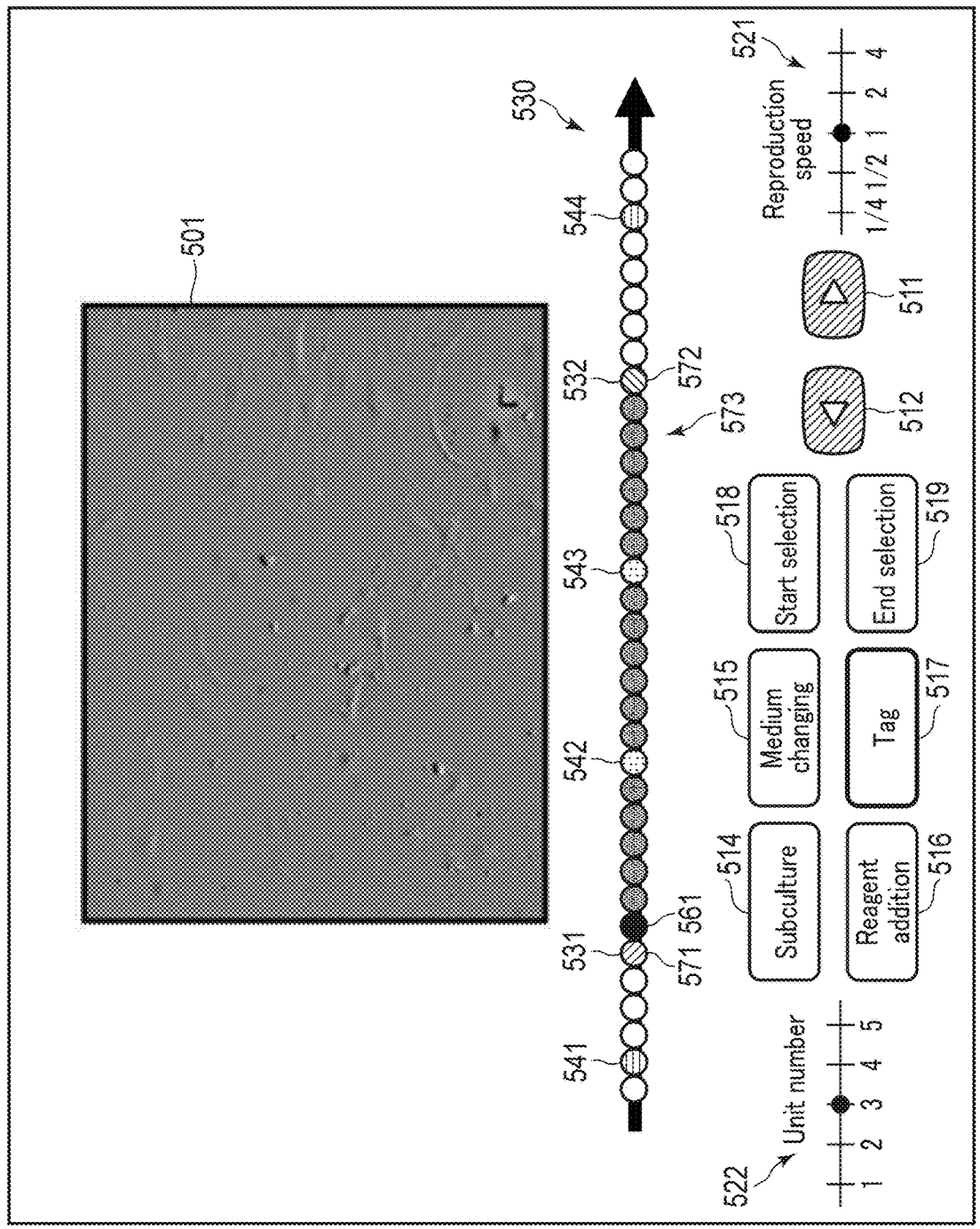
FIG. 10B is a view illustrating an outline of an example of the display screen according to the embodiment.

FIG. 10A shows an example in which "3" is selected as a unit number in the unit number adjustment display 522. In addition, the tag icon 517 is selected. When the reproduction icon 511 is selected in this state, the reproduction selected images 573 are determined as shown in FIG. 10B. That is, the first subculture operation tagged image 531 as a tagged image immediately before the selected image 561 is selected as the starting image 571. Since numeral 3 is selected as a unit number, the second subculture operation tagged image 532 as the third tagged image from the starting image 571 is selected as the ending image 572. In other words, the images in three units of interval between one tagged image and another tagged image are selected as the reproduction selected images 573. Herein, the three units of interval include an interval from the first subculture operation tagged image 531 to the second medium changing tagged image 542, an interval from the second medium changing tagged image 542 to the third medium changing tagged image 543, and an interval from the third medium changing tagged image 543 to the second subculture operation tagged image 532.

[Operation of Observation System]

Figure 11:
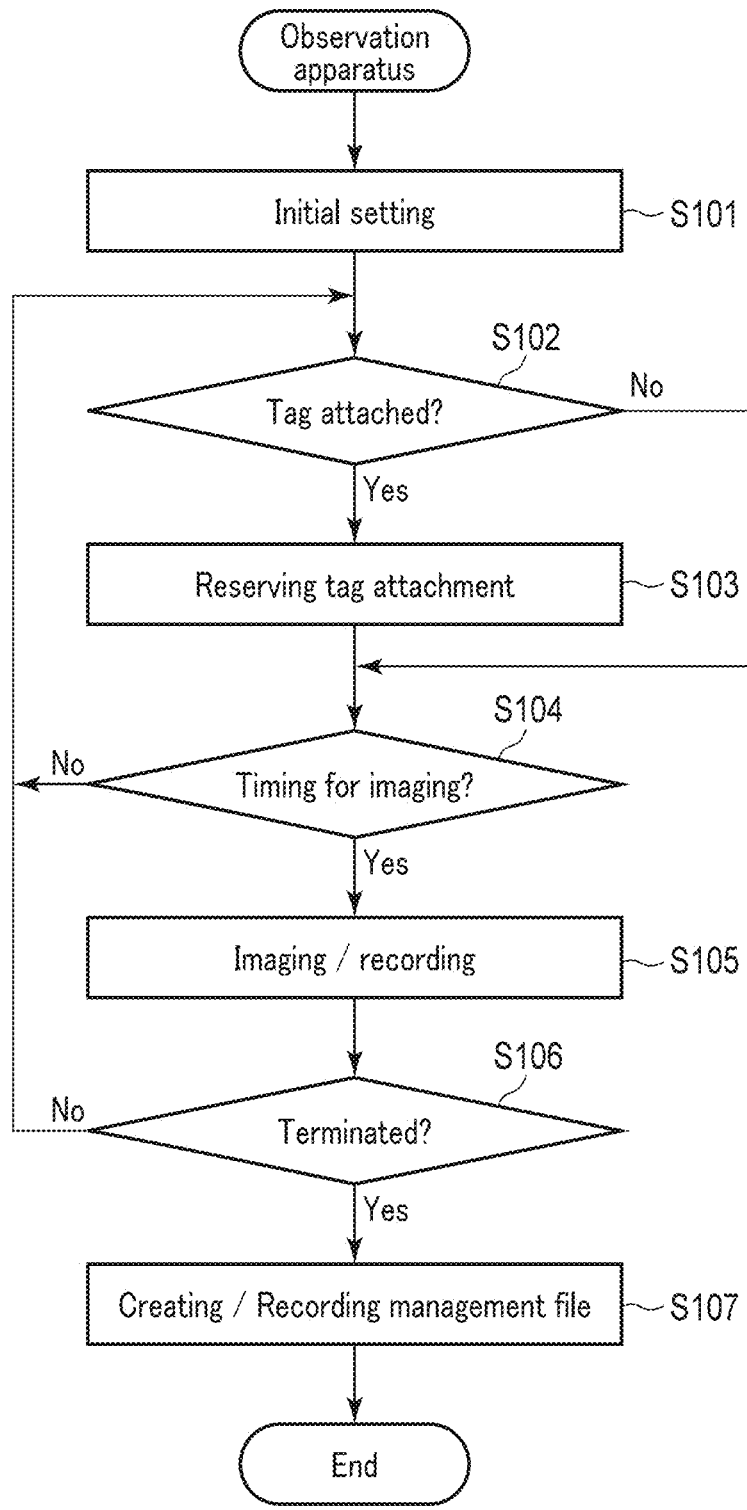
FIG. 11 is a flowchart illustrating an outline of an example of an operation of an observation apparatus according to the embodiment.

The observation operation performed by the observation apparatus 200 to acquire images of the sample 300 will be described with reference to the flowchart shown in FIG. 11. In step S101, the processor 222 of the observation apparatus 200 performs various types of initial setting. The initial setting may include imaging conditions such as a focal length, a focus position, an aperture value, an exposure time, etc. The initial setting may include imaging timing including an imaging time interval, the number of times imaging is performed, a duration of observation operation, etc.

In step S102, the processor 222 determines whether or not to attach a tag to an image obtained by imaging. For example, the processor 222 determines to attach a tag when receiving input through the input interface 218, for example, input of the fact that the subculture operation has been performed, the fact that the medium changing operation has been performed, the fact that the operation of adding reagent, etc., has been performed, etc. When no tag is attached, the process proceeds to step S104. On the other hand, when a tag is attached, the process proceeds to step S103.

In step S103, the processor 222 makes a reservation for tag attachment. That is, the processor 222 determines to attach tag information to image data obtained by next imaging. As a result, when image data is obtained by the next imaging operation, information relating to a tag is recorded in association with the obtained image data.

In step S104, the processor 222 determines whether the timing to perform imaging has come or not. For example, when the timing for imaging set in step S101 comes, the processor 222 determines that the timing for imaging has come. In the case of determination that the timing for imaging has not come yet, the process returns to step S102. That is, the processor 222 stands by while checking input to the input interface 218. In step S104, in the case of determination that the timing for imaging has come, the process proceeds to step S105.

In step S105, the processor 222 causes the imaging unit 216 to perform an imaging operation. Image data is created by this imaging operation. The processor 222 records the obtained image data in the recording device 217 of the observation apparatus 200. If attachment of tag information is reserved, the processor 222 attaches the tag information to the image data and records this image data in the recording device 217.

In step S106, the processor 222 determines whether or not to terminate a series of observation operations. For example, when the duration of the observation operation set in step S101 has elapsed, the processor 222 determines to terminate the observation operation. When the observation operation is not terminated, the process returns to step S102 and the above-described operation is repeated. When termination of the observation operation is terminated, the process proceeds to step S107.

In step S107, the processor 222 creates a management file indicating the association of image data, etc., obtained by a series of observation operations, and records this management file together with the image data in the recording device 217 of the observation apparatus 200. This management file and data on a plurality of images constitute the image group data 400 described above.

In the example described above, upon receipt of a tag attachment operation, such as an operation to the input interface 218, tag information is added to image data obtained immediately after this operation. However, this example is not a limitation. For example, when a tag attachment operation is performed, tag information may be attached to the image data positioned immediately before this operation. Furthermore, tag information may be recorded separately from image data. In such a case, tag information serves as information that clarifies a time relationship between image data obtained before an operation and image data obtained after an operation, the time relationship including a time when an operation is performed on the input interface 218. When tag information is not attached to image data, the screens shown as examples in FIGS. 4A to 10B may be changed as appropriate.

Next, the image reproducing process performed in the image reproducing device 110 will be described with reference to a flowchart shown in FIG. 12. In the image reproducing process, the image reproducing device 110 acquires image data from the observation apparatus 200 and causes the display 154 to display images based on user's operation.

In step S201, the processor 112 of the image reproducing device 110 acquires the image group data 400 including data on a plurality of images, a management file, etc., from the recording device 217 of the observation apparatus 200.

In step S202, the processor 112 acquires input by a user through the input interface 152, and identifies which image corresponds to the selected image 561 being currently selected.

In step S203, the processor 112 outputs to the display 154, screen data that causes the selected image to be displayed in the image display area 501, thereby causing the display 154 to perform screen display.

In step S204, the processor 112 determines whether one of the starting image and the ending image is selected or not, depending on whether one of the start selection icon 518 and the end selection icon 519 is selected. When neither the starting image nor the ending image is selected, the process proceeds to step S206. On the other hand, when the starting image or the ending image is selected, the process proceeds to step S205. In step S205, the processor 112 sets the starting image 571 or the ending image 572 based on the above selection. Thereafter, the process proceeds to step S206.

In step S206, the processor 112 specifies which one of the subculture icon 514, the medium changing icon 515, the reagent addition icon 516, and the tag icon 517 is selected, to acquire information relating to a type of a tag serving as a criterion to select the reproduction selected images 573.

In step S207, the processor 112 determines what operation is made by a user on the unit number adjustment display 522, to acquire a selected unit number. In step S208, the processor 112 determines what operation is made by a user on the reproduction speed adjustment display 521, to acquire a selected reproduction speed.

In step S209, the processor 112 determines whether or not to perform a reproduction operation. That is, the processor 112 determines whether one of the reproduction icon 511 and the reverse reproduction icon 512 has been selected or not by a user. In the case of determination that the reproduction operation is not performed, the process returns to step S202. That is, the processor 112 repeatedly performs identification and display of a selected image, identification of a starting image and an ending image, acquisition of a tag type, acquisition of a unit number, and acquisition of a reproduction speed. On the other hand, in step S209, in the case of determination that the reproduction operation is performed, the process proceeds to step S210.

In step S210, the processor 112 determines a range of images to be reproduced from images that are present along time series. That is, the processor 112 identifies the starting image 571 and the ending image 572 as described above, to determine the reproduction selected images.

In step S211, the processor 112 outputs to the display 154, screen data that causes a plurality of reproduction selected images to be sequentially displayed in the image display area 501. As a result, a time-lapse movie image is displayed on the display 154. When the display of the time-lapse movie image ends, the process returns to step S202. That is, the process from steps S202 to S211 described above is repeated.

[Feature of Observation System]

In the observation system 1 according to the present embodiment, when image data is acquired by imaging with the observation apparatus 200, a tag corresponding to the operation is attached in association with the image data. The image reproducing device 110 that reproduces image group data including tags associated with operations is capable of selecting and reproducing part of images included in the image group data. In particular, the image reproducing device 110 enables a user to select which image to reproduce, based on a tag associated with an operation. A range of images associated with operations such as a subculture operation, a medium changing operation, a reagent adding operation, etc., is of special interest to a user. For example, a group of images obtained between a subculture operation and another subculture operation is of interest to a user who desires to check the process of cell proliferation. Moreover, a group of images obtained after addition of a reagent is of interest to a user who desires to check the influence of the added reagent on cells, etc. The image reproducing device 110 according to the present embodiment enables a user to appropriately select a group of images that are of interest, in connection with a simple operation being performed by the user. That is, a user can reproduce a group of images of interest by performing a simple operation.

[Modification]

A modification of the above embodiment will be described. Herein, differences from the above embodiment will be described. The same symbols will be used to denote similar structural elements, and a description of such structural elements will be omitted. In the above embodiment, a single image is displayed in a single image display area 501. On the other hand, in this modification, a plurality of images are displayed in the image display area 501.

In the example described in the above embodiment, the observation apparatus 200 acquires images of one part of the sample 300 over time. On the other hand, in this modification, the observation apparatus 200 acquires images of a plurality of parts of the sample 300. For this, in the observation apparatus 200, for example, the imaging unit 216 moves to sequentially image respective parts of the sample 300. The observation apparatus 200 repeats this imaging at predetermined intervals, for example, and acquires time-lapse images of the respective parts. Alternatively, the observation apparatus 200 includes a plurality of imaging units 216 and simultaneously images respective parts of the sample 300. The observation apparatus 200 repeats this imaging at predetermined intervals, for example, and acquires time-lapse images of the respective parts.

Figure 13:
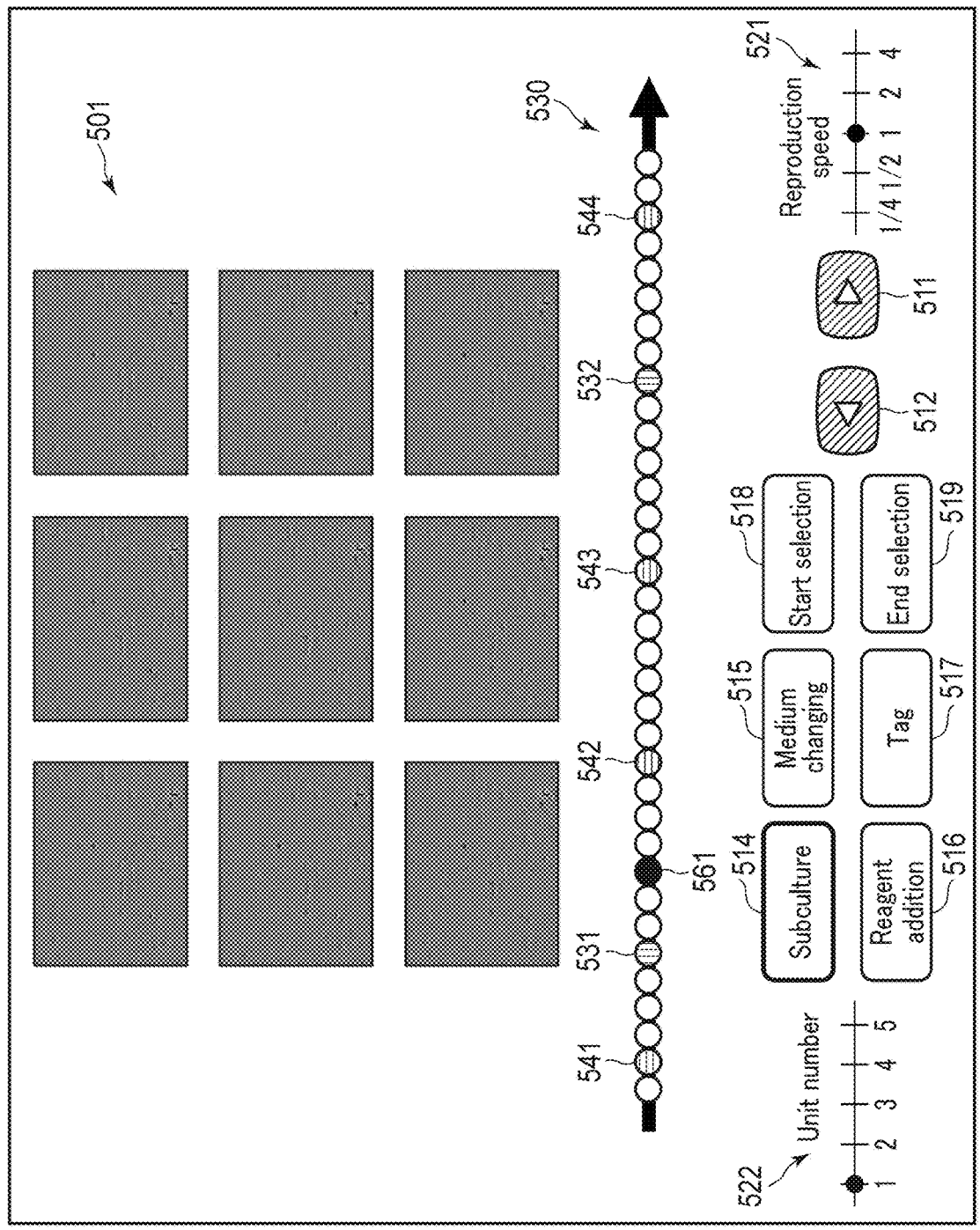
FIG. 13 is a view illustrating an outline of an example of a display screen according to a modification.

FIG. 13 shows an example of the reproduction screen 500 displayed by the image reproducing device 110 according to this modification. As shown in FIG. 13, the image display area 501 displays a list of images of different parts of the sample 300. For example, when the reproduction icon 511 is selected to reproduce a time-lapse movie image, a plurality of images included in the image display area 501 are reproduced simultaneously as a movie image.

When one of a plurality of images included in the image display area 501 is selected by a user, the selected image may be enlarged and displayed on the entire surface of the image display area 501 as in the above embodiment.

This modification can also produce a similar effect to that of the above embodiment.

In the examples described in the above embodiment and its modification, a subculture operation, a medium changing operation, and a different operation such as addition of a reagent have been described as an operation for which a tag is attached. However, a tag to be attached is not necessarily limited to those three types. For example, a type of a tag attached to images may be any one or two of a subculture operation, a medium changing operation, and a different operation. In a mode in which a tag to be attached to images has only a single type selected from a subculture operation, a medium changing operation, and a different operation, the observation apparatus 200 may include as the input interface 218, only one button switch corresponding to this single type selected from a subculture operation, a medium changing operation, and a different operation. In a mode in which a tag to be attached to images has two types selected from a subculture operation, a medium changing operation, and a different operation, the observation apparatus 200 may include as the input interface 218, two button switches corresponding to these two types selected from a subculture operation, a medium changing operation, and a different operation. The same applies even if a tag has four or more types. In a mode in which a tag is attached to images without distinguishing a type of operation, the observation apparatus 200 may include only one button switch as the input interface 218.

When a button switch as the input interface 218 provided in the observation apparatus 200 is pressed to attach an operation tag, the observation apparatus 200 may temporarily halt the observation of the sample 300. In this case, the observation apparatus 200 may resume the observation of the sample 300 in reaction to any button switch being pressed again. For example, in the observation operation described with reference to FIG. 11, assumed that it is determined in step S102 that any button switch of the input interface 218 has been pressed. In this case, after step S103, the process may stand by until any button switch is pressed again, and may proceed to step S104 when it is determined that any button switch is pressed again.

The reproduction screen 500, the method of selecting the reproduction selected images 573, etc., in the above description are examples. The reproduction screen may be any screen. The elements shown in FIG. 4A, etc. may be deleted as appropriate, added as appropriate, and freely changed in terms of arrangement and size. Images selected as the reproduction selected images 573 may be set as appropriate.

Of the techniques described in the above, the controls described using the flowcharts are realized as programs. The programs may be stored in a recording medium or a recording unit. Recording in a recording medium or a recording unit is performed by various ways. For example, recording may be performed at the time of product shipment, may be performed using a distributed recording medium, or may be performed by download on the Internet.

Each process described above may be realized by artificial intelligence composed by deep learning, etc. For example, learning user's selection of images that the user desires to reproduce may enable even artificial intelligence to appropriately select images desired by the user, using tag information, for example.

Additional advantages and modifications will readily occur to those skilled in the art. Therefore, the embodiment in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An observation system comprising:
 an imaging unit configured to acquire a plurality of images relating to a biological sample along time series;
 an input interface to which an operation by a user is input; and
 one or more processors configured to:
  acquire image group data including the plurality of images acquired by the imaging unit, and tag information per operation on the biological sample, wherein the tag information is attached in accordance with information that an operation is performed on the biological sample, and input by the user through the input interface when at least one of the images is acquired;
  select, from the plurality of images using the tag information, images to be reproduced along the time series as reproduction selected images; and
  output to a display, data relating to the images for the reproduction selected images to be reproduced along time series.

2. The observation system according to claim 1, wherein the operation on the biological sample is at least one of a subculture operation on the biological sample, a medium changing operation, and an operation of adding a reagent to a medium.

3. The observation system according to claim 1, wherein the one or more processors are configured to:
 further acquire a selection operation by the user to select one of the images, as a user selected image; and
 select images including the user selected image, as the reproduction selected images.

4. The observation system according to claim 3, wherein the one or more processors are configured to perform one of:
 select, as the reproduction selected images, images ranging from an image that is associated with the tag information and is obtained immediately before the user selected image, to an image that is associated with the tag information and is obtained immediately after the user selected image or a last image of the plurality of images; and
 select, as the reproduction selected images, images ranging from an image that is associated with the tag information and is obtained immediately before the user selected image or a first image of the plurality of images, to an image that is associated with the tag information and is obtained immediately after the user selected image.

5. The observation system according to claim 3, wherein the one or more processors are configured to output a relation between the image and the tag information and information on the plurality of images to the display in order for the user to select the user selected image.

6. The observation system according to claim 3, wherein the one or more processors are configured to select the user selected image as a first image or a last image of the reproduction selected images, in accordance with an operation by the user.

7. The observation system according to claim 1, wherein the tag information is attached to the image acquired immediately before or immediately after the input interface is operated by the user.

8. The observation system according to claim 1, wherein the tag information is information that is recorded separately from the image and indicative of a time relationship between the image obtained before the input interface is operated by the user and the image obtained after the input interface is operated by the user.

9. An image reproducing device comprising:
 one or more processors configured to:
  acquire image group data including a plurality of images relating to a biological sample along time series, and tag information on at least one tag that relates to an operation on the biological sample and is associated with at least part of the images;

acquire a unit number through input by a user, the unit number indicating a number of units on a condition that one unit is set to an interval between the tag information and the next tag information along the time series;

select, from the plurality of images, using the tag information and in units corresponding to the input unit number, images to be reproduced along the time series as reproduction selected images; and output to a display, data relating to the images for the reproduction selected images to be reproduced along time series.

10. A method comprising:

one or more processors configured to:

acquiring image group data including a plurality of images relating to a biological sample, acquired by an imaging unit along time series, and tag information per operation on the biological sample,
wherein the tag information is attached in accordance with information that an operation is performed on the biological sample, and input by a user through an input interface when at least one of the images is acquired;

selecting from the plurality of images using the tag information, images to be reproduced along the time series as reproduction selected images; and outputting to a display, data relating to the images for the reproduction selected images to be reproduced along time series.

* * * * *